US011191730B2

(12) United States Patent
Shah et al.

(10) Patent No.: US 11,191,730 B2
(45) Date of Patent: *Dec. 7, 2021

(54) ABUSE RESISTANT FORMS OF IMMEDIATE RELEASE HYDROMORPHONE, METHOD OF USE AND METHOD OF MAKING

(71) Applicant: OHEMO LIFE SCIENCES INC., Juncos, PR (US)

(72) Inventors: Manish S. Shah, West Caldwell, NJ (US); Ray J. DiFalco, Ridgewood, NJ (US)

(73) Assignee: OHEMO LIFE SCIENCES INC., Juncos, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/536,391

(22) Filed: Nov. 7, 2014

(65) Prior Publication Data

US 2015/0064245 A1 Mar. 5, 2015

Related U.S. Application Data

(63) Continuation of application No. 13/040,953, filed on Mar. 4, 2011, now Pat. No. 11,045,422, which is a continuation of application No. 12/680,701, filed as application No. PCT/US2008/072914 on Aug. 12, 2008, now Pat. No. 10,736,850.

(Continued)

(51) Int. Cl.

| | |
|---|---|
| *A61K 47/38* | (2006.01) |
| *A61K 9/28* | (2006.01) |
| *A61P 25/04* | (2006.01) |
| *A61K 9/20* | (2006.01) |
| *A61K 9/24* | (2006.01) |
| *A61K 31/138* | (2006.01) |
| *A61K 31/437* | (2006.01) |
| *A61K 31/4458* | (2006.01) |
| *A61K 9/48* | (2006.01) |
| *A61K 31/485* | (2006.01) |
| *A61K 9/16* | (2006.01) |
| *A61K 9/50* | (2006.01) |
| *A61K 47/32* | (2006.01) |
| *A61K 47/34* | (2017.01) |

(52) U.S. Cl.
CPC ............ *A61K 9/2086* (2013.01); *A61K 9/16* (2013.01); *A61K 9/1617* (2013.01); *A61K 9/1623* (2013.01); *A61K 9/1641* (2013.01); *A61K 9/1652* (2013.01); *A61K 9/1676* (2013.01); *A61K 9/209* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 9/2081* (2013.01); *A61K 9/28* (2013.01); *A61K 9/2846* (2013.01); *A61K 9/2886* (2013.01); *A61K 9/4808* (2013.01); *A61K 9/4858* (2013.01); *A61K 9/4866* (2013.01); *A61K 9/4891* (2013.01); *A61K 9/5026* (2013.01); *A61K 9/5031* (2013.01); *A61K 9/5042* (2013.01); *A61K 9/5047* (2013.01); *A61K 9/5078* (2013.01); *A61K 31/138* (2013.01); *A61K 31/437* (2013.01); *A61K 31/4458* (2013.01); *A61K 31/485* (2013.01); *A61K 47/32* (2013.01); *A61K 47/34* (2013.01); *A61K 47/38* (2013.01); *Y10T 156/10* (2015.01)

(58) Field of Classification Search
CPC .... A61K 9/209; A61K 9/2031; A61K 9/2054; A61K 9/2086; A61K 9/2846; A61K 9/2886; A61K 9/4891; A61K 31/485
USPC ....... 424/400, 440, 457, 463, 464, 472, 482, 424/489, 490, 497, 501; 427/2.14, 2.21; 514/259.3, 282, 317, 468, 629, 646, 652; 546/44, 45, 238; 564/349, 443; 156/60; 544/281
See application file for complete search history.

(56) References Cited

U.S. PATENT DOCUMENTS

| | | | |
|---|---|---|---|
| 5,206,030 A | | 4/1993 | Wheatley et al. |
| 5,273,760 A | * | 12/1993 | Oshlack ............... A61K 9/2866 424/461 |

(Continued)

FOREIGN PATENT DOCUMENTS

| | | |
|---|---|---|
| CA | 2 554 697 A1 | 4/2007 |
| CA | 2764517 A1 * 12/2010 | ........... A61K 9/1617 |

(Continued)

OTHER PUBLICATIONS

Evonik, Eudragit® NE 30 D, Specification and Test Methods, (May 2014), 5 pages.*

(Continued)

*Primary Examiner* — Ernst V Arnold
(74) *Attorney, Agent, or Firm* — Juneau & Mitchell; William E. Beaumont

(57) ABSTRACT

An abuse resistant oral pharmaceutical composition, comprising: a barrier layer, comprising a first polymer; a diffusion layer, comprising a second polymer, substantially covering the barrier layer, wherein the diffusion layer is bonded to the barrier layer and comprises a drug that is substantially homogeneously distributed within the second polymer and diffuses from the diffusion layer within the gastrointestinal (GI) tract; and optionally an expansion layer comprising an expandable polymer, wherein the expansion layer is substantially covered by the barrier layer. Methods of making the same and methods of using the same are also provided.

15 Claims, 4 Drawing Sheets

Related U.S. Application Data

(60) Provisional application No. 60/955,584, filed on Aug. 13, 2007.

(56) References Cited

U.S. PATENT DOCUMENTS

| | | | |
|---|---|---|---|
| 5,286,493 A * | 2/1994 | Oshlack | A61K 9/2846 424/468 |
| 5,395,626 A | 3/1995 | Kotwal et al. | |
| 5,783,212 A * | 7/1998 | Fassihi | A61K 9/2086 424/464 |
| 5,866,161 A | 2/1999 | Childers et al. | |
| 5,958,459 A | 9/1999 | Chasin et al. | |
| 6,024,982 A * | 2/2000 | Oshlack | A61K 9/2866 424/468 |
| 6,066,339 A | 5/2000 | Stark et al. | |
| 6,309,668 B1 | 10/2001 | Bastin et al. | |
| 6,310,072 B1 | 10/2001 | Smith et al. | |
| 6,419,954 B1 | 7/2002 | Chu et al. | |
| 6,911,217 B1 | 6/2005 | Gren et al. | |
| 2003/0068371 A1 | 4/2003 | Oshlack et al. | |
| 2003/0068375 A1 | 4/2003 | Wright et al. | |
| 2003/0092724 A1 | 5/2003 | Kao et al. | |
| 2003/0118641 A1 | 6/2003 | Maloney et al. | |
| 2003/0157167 A1 | 8/2003 | Kao et al. | |
| 2003/0180359 A1 | 9/2003 | Vergnault et al. | |
| 2004/0052731 A1 | 3/2004 | Hirsh et al. | |
| 2004/0092542 A1 | 5/2004 | Oshlack et al. | |
| 2004/0131552 A1 * | 7/2004 | Boehm | 424/10.1 |
| 2004/0161382 A1 | 8/2004 | Yum et al. | |
| 2004/0228802 A1 | 11/2004 | Chang et al. | |
| 2005/0020613 A1 | 1/2005 | Boehm et al. | |
| 2005/0080012 A1 | 4/2005 | Mickle et al. | |
| 2005/0112067 A1 | 5/2005 | Kumar et al. | |
| 2005/0191349 A1 | 9/2005 | Boehm et al. | |
| 2005/0214223 A1 | 9/2005 | Bartholomaeus et al. | |
| 2005/0220715 A1 | 10/2005 | Lin | |
| 2005/0245483 A1 | 11/2005 | Brogmann et al. | |
| 2005/0266080 A1 | 12/2005 | Desai et al. | |
| 2005/0281748 A1 | 12/2005 | Hirsh et al. | |
| 2006/0014697 A1 | 1/2006 | Mickle et al. | |
| 2006/0104909 A1 | 5/2006 | Vaghefi et al. | |
| 2006/0110327 A1 | 5/2006 | Emigh et al. | |
| 2006/0165602 A1 | 7/2006 | Galer et al. | |
| 2007/0020339 A1 | 1/2007 | Bear | |
| 2007/0128269 A1 | 6/2007 | Gervais et al. | |
| 2007/0259045 A1 | 11/2007 | Mannion et al. | |
| 2007/0269505 A1 | 11/2007 | Flath et al. | |
| 2008/0085305 A1 | 4/2008 | Baichwal et al. | |
| 2009/0018043 A1 * | 1/2009 | Beckers | B30B 11/06 510/224 |
| 2009/0022798 A1 | 1/2009 | Rosenberg et al. | |
| 2009/0081290 A1 | 3/2009 | Mckenna et al. | |
| 2009/0082466 A1 | 3/2009 | Babul | |
| 2010/0015223 A1 | 1/2010 | Cailly-Dufestel et al. | |
| 2010/0099696 A1 | 4/2010 | Soscia et al. | |
| 2010/0221324 A1 | 9/2010 | Petereit et al. | |
| 2010/0226978 A1 | 9/2010 | Petereit et al. | |
| 2012/0003311 A9 | 1/2012 | Yoshitake et al. | |
| 2012/0202839 A1 | 8/2012 | Emigh et al. | |
| 2015/0366801 A1 * | 12/2015 | Jacob | A61J 3/06 424/465 |

FOREIGN PATENT DOCUMENTS

| | | |
|---|---|---|
| DE | 102006051020 A1 | 4/2008 |
| EP | 0682945 A2 | 11/1995 |
| FR | 2787715 A1 | 6/2000 |
| WO | WO 95/20947 A1 | 8/1995 |
| WO | WO 95/25506 A1 | 9/1995 |
| WO | WO 00/27364 A1 | 5/2000 |
| WO | WO 03/013479 A1 | 2/2003 |
| WO | WO 2004/037259 A1 | 5/2004 |
| WO | WO 2005/055981 A2 | 6/2005 |
| WO | WO 2006/079550 A2 | 8/2006 |
| WO | WO 2008/049657 A2 | 5/2008 |

OTHER PUBLICATIONS

Sigma-Aldrich, Chemicals—Technical Library, Particle Size Conversion Table, [Retrieved from internet <URL: http://www.sigmaaldrich.com/chemistry/stockroom-reagents/learning-center/technical-library/particle-size-conversion.html >], [Downloaded Sep. 23, 2017], 2 pages.*

Desphande et al., Bi-Layer Tablets—An Emerging Trend: A Review; International Journal of Pharmaceutical Sciences and Research (IJPSR) (2011), vol. 2(10): 2534-2544 (11 pages total).*

Zacour et al., Correlating bilayer tablet delamination tendencies to micro-environmental thermodynamic conditions during pan coating, Drug Development and Industrial Pharmacy (2014), 40(6): 829-837, (publ. on line, May 3, 2013) (10 pages total).*

Abbaspour et al., "Preparation and characterization of ibuprofen pellets based on Eudragit RS PO and RL PO or their combination," International Journal of Pharmaceutics, 2005, 303:88-94.

Babak et al., "Impact of bulk and surface properties of some biocompatible hydrophobic polymers on the stability of methylene chloride-in-water mini-emulsions used to prepare nanoparticles by emulsification—solvent evaporation," Colloids and Surfaces B: Biointerfaces, 2007, 59:194-207.

Chithaluru et al., "Formulation and Invitro Evaluation of Sustained Release Matrix Tablets of Losartan Potassium," Asian Journal of Pharmaceutical and Clinical Research, 2011, vol. 4, issue 3, pp. 18-22.

Cozzolino et al., "Dye release behavior from polyvinyl alcohol films in a hydro-alcoholic medium: Influence of physicochemical heterogeneity," Colloids and Surfaces A: Physicochemical and Engineering Aspects, 2012, 403:45-53.

Murtaza, "Ethylcellulose Microparticles: A Review," Acta Poloniae Pharmaceutica—Drug Research, vol. 69, No. 1, pp. 11-22 (2012).

"Avinza (morphine sulfate) Capsule, Extended Release [Ligand Pharmaceuticals Incorporated]." Daily Med. National Institutes of Health, Web. Jan. 7, 2013, 15 pages.

"Eudragit® RS PO." Evonik Industries AG, Web. Apr. 25, 2012. <http://eudragit.evonik.com/product/eudragit/en/products-services/eudragit-products/sustained-release-fc 2 pages.

"Opadry Complete Film Coating System." Colorcon, Web. Sep. 25, 2012. <http://www.colorcon.com/products/coatings/immediate-release/Opadry>. 2 pages.

"Roxicodone® (Oxycodone Hydrochloride Tablets USP)." Daily Med. National Institutes of Health, Web. May 7, 2013. <http://dailymed.nlm.nih.gov/dailymed/archives/fdaDrugInfo.cfm?archiveid=12847>. 19 pages.

"Substrate" Chambers 21st Century Dictionary. London: Chambers Harrap Publishers Limited, 2001. Credo Reference. Web. <www.credoreference.com/entry/chambdict/substrate>. 2 pages.

"Oxycontin® (Oxycodone HCl Controlled-Release Tablets)" Monograph, Purdue Pharma, 2007, accessed at http://accessdata.fda.gov/drugsatfda_docs/label/2009/020553s060lbl.pdf. 32 pages.

14. Opana Er (oxymorphone Hydrochloride) Tablet, Extended Release Tablets [Endo Pharmaceuticals]. Daily Med. National Institutes of Health, Web. Feb. 22, 2013. <http://dailymed.nlm.nih.gov/dailymed/lookup.cfm?setid=545cea18-11ad-4881-b184-6f8bcc7908e4>. 24 pages.

Amabile et al. "Overview of Oral Modified-Release Opioid Products for the Management of Chronic Pain," Ann Pharmacother, 2006; 40:1327-1335.

Bajpai et al. "Responsive Polymers in Controlled Drug Delivery," Progress in Polymer Science 2008;33:1088-1118.

Crowley et al. "Drug-Excipient Interactions," Pharmaceutical Technology, 2001, pp. 1-6.

Fisher. "Appendix E." A Chronic Pain Management Manual: A Guide for Those Who Suffer and Those Who Treat Pain. Lincoln, NE: Writer's Club, 2002, pp. 112-113, 4 pages.

Food and Drug Administration. U.S. Department of Health and Human Services. Guidance for Industry: Dissolution Testing of

(56) References Cited

OTHER PUBLICATIONS

Immediate Release Solid Oral Dosage Forms. Web: Center for Drug Evaluation and Research, Aug. 1997. 17 pages.
Fujita et al., "Methodologies for regulation of intestinal absorption of biologically active peptides," Nippon Rinsho, Mar. 1998; 56(3): 589-594 (Abstract). 2 pages.
Gimbel et al. "The Efficacy and Safety of Oral Immediate-Release Oxymorphone for Postsurgical Pain," Anesth Analg, 2004; 99: 1472-1477.
Kral et al. "Oxycodone Safety Handout for Patients." Pain Treatment Topics, Jun. 2007. Web. 7 pages.
Lenaerts et al. "Cross-linked high amylose starch for controlled release of drugs: recent advances," Journal of Controlled Release, 1998; 53: 225-234.
Meijerman et al. "Herb-Drug Interactions in Oncology: Focus on Mechanisms of Induction," The Oncologist, 2006; 11:742-752.
Overgaard et al. "Patient's evaluation of shape, size and colour of solid dosage forms," Pharm World Sci, 2001; 23(5): 185-188. 8 pages.
Page et al. "Innovations in oral gene delivery: challenges and potentials," DDT, 2001; 6(2): 92-101.
Savage et al. "Challenges in Using Opioids to Treat Pain in Persons with Substance Use Disorders," Addict. Sci. Clin. Pract., 2008; 4(2): 4-25.
Solinis et al. "Release in ketoprofen enantiomers from HPMC K100M matrices—diffusion studies," International Journal of Pharmaceutics, 2002; 239:61-68.
Van Zee, "The Promotion and Marketing of OxyContin: Commercial Triumph, Public Health Tragedy," American Journal of Public Health, 2009; 99:221-227.

\* cited by examiner

ABUSE RESISTANT FORMS OF IMMEDIATE RELEASE HYDROMORPHONE, METHOD OF USE AND METHOD OF MAKING

CROSS-REFERENCE TO RELATED APPLICATION

This application is a continuation of U.S. patent application Ser. No. 13/040,953, filed on Mar. 4, 2011, which is a continuation of U.S. patent application Ser. No. 12/680,701, filed on Sep. 16, 2010, which is national stage entry of International Application No. PCT/US08/72914, having an international filing date of Aug. 12, 2008 and claiming priority to U.S. Provisional Patent Application No. 60/955,584, filed on Aug. 13, 2007, the disclosure of each of which is hereby incorporated in its entirety by reference.

BACKGROUND OF THE INVENTION

The present invention is generally in the field of pharmaceutical compositions, and specifically relates to compositions that are designed to reduce the potential for improper administration of medications and their use in a non-indicated or non-prescribed manner. The present invention can comprise any drug, especially medications that are subject to abuse. More specifically, it pertains to pain medications, medications to reduce or eliminate anxiety attack (psychotherapeutic drugs), stimulants and sleeping pills. With these general type drugs there is the potential of abuse that may result in drug overdose, addiction, suboptimal efficacy, and/or death.

In particular, the present invention relates to an abuse resistant composition (for, e.g., pain medication, anxiety attack medication, sleeping medication or stimulants), having, but not limited to, a diffusion layer and a barrier layer; use of such a composition in a dosage form to treat diseases or conditions; and a method of making an abuse deterrent composition having a diffusion layer and a barrier layer. In some embodiments, the composition also comprises an expansion layer.

Opioid agonists are substances that act by attaching to specific proteins called opioid receptors, which are found in the brain, spinal cord, and gastrointestinal tract. When these drugs attach to certain opioid receptors in the brain and spinal cord they can effectively block the transmission of pain messages to the brain. Opioid analgesics such as oxycodone, morphine, oxymorphone, hydrocodone and hydromorphone are successful and therapeutically useful pain medications. Unfortunately, they also pose a severe threat for willful abuse due to their ability to alter mood and/or cause a sense of euphoria (a "high"). Currently available sustained release formulations of such drugs, which contain a relatively large amount of drug substance meant to be released from the formulation over an extended time period, are particularly attractive to abusers since the sustained release action can be destroyed by crushing or grinding the formulation. The resulting material (i.e., the crushed formulation) can no longer control the release of drug. Depending on the drug substance, abusers can then (1) snort the material, (2) swallow the material or (3) dissolve the material in water or alcohol and subsequently inject it intravenously. The dose of drug contained in the formulation is thus absorbed immediately through the nasal or GI mucosa (for snorting or swallowing, respectively) or is administered in a bolus to the systemic circulation (for IV injection).

These abuse methods result in the rapid bioavailability of relatively high doses of drug contained in a single tablet or capsule, giving the abuser a "high." The sense of euphoria, or "high," is highly correlated with the peak serum concentration of the drug substance (Cmax). Although such a high serum concentration can be obtained from taking several immediate release or sustained release tablets at once, abusers are deterred from doing so because multiple tablets are harder to come by and, maybe more importantly, the very high dose associated with taking several tablets at once is associated with an severely increased risk of overdose (typically a function of high serum levels of the drug substance over prolonged periods of time; resulting in a high area under the curve: the integral of the serum concentration over time, also known by the acronym "AUC"). In order to reduce the risk of overdose, the typical abuser will prefer to obtain a high peak serum concentration from a single tablet or capsule. In the scientific terminology of a pharmacologist, the typical abuser appears to maximize Cmax while minimizing AUC, or alternatively, to maximize the Cmax/AUC ratio.

In some cases, abusers consume alcohol with immediate and/or extended release formulations to reach a "high" more quickly. Abusers sometimes place the formulation in water or alcohol, in order to extract the drug in an accelerated fashion. The coadministration of these liquids is known to sometimes decrease the time after drug administration in which the peak plasma concentration and Cmax are reached. Sometimes abusers place the formulation into other solvents such as freon, methylene chloride, ethanol, and acetone, in order to extract the drug, which can then be injected. Another technique used by abusers to extract drug from a dosage form such as a tablet is wiping the coating off of the tablet, crushing the tablet into a fine powder, placing the powder into sterile water, and then drawing the liquid into a syringe. In addition, the dosage form can be generally physically compromised by crushing, grinding, and chewing.

Since relatively simple methods (crushing, grinding, chewing and/or dissolution in water or alcohol) can be used to transform a single extended release tablet or capsule formulation into an abusable form, these conventional dosage forms provide virtually no deterrent to a potential abuser.

The FDA recently strengthened the warnings and precautions sections in the labeling of OXYCONTIN® (oxycodone HCl controlled-release) Tablets, a narcotic drug approved for the treatment of moderate to severe pain, because of continuing reports of abuse and diversion. OXYCONTIN® contains oxycodone HCl (available in 10, 20, 40, 80, and 160 mg strengths), an opioid agonist with an addiction potential similar to that of morphine. OXYCONTIN® is supplied in a controlled-release dosage form and is intended to provide up to 12 hours of relief from moderate to severe pain. The FDA warning specifically states that the tablet must be taken whole and only by mouth. When the tablet is chewed or crushed and its contents are swallowed, snorted into the nostrils or dissolved and subsequently injected intravenously, the controlled release mechanism is destroyed and a dangerous dose of oxycodone becomes bioavailable, which is potentially lethal to users of this product, in particular first time users.

In recent years, there have been numerous reports of oxycodone diversion and abuse in several states. For example, DEA's Office of Diversion Control reported 700 OXYCONTIN® thefts in the U.S. between January 2000 and June 2001. Some of these reported cases have been associated with serious consequences, including death.

Oxycodone is a controlled substance in Schedule II of the Controlled Substances Act (CSA), which is administered by the Drug Enforcement Administration (DEA). Despite the fact that Schedule II provides the maximum amount of control possible under the CSA for approved drug products, in practice it is difficult for law enforcement agencies to control the diversion or misuse of legitimate prescriptions. Although abuse, misuse, and diversion are potential problems for all opioids, including oxycodone, opioids are a very important part of the medical armamentarium for the management of pain when used appropriately under the careful supervision of a physician. Currently available formulations for such drugs are designed for oral administration but do not include mechanisms to prevent or retard improper methods of administration such as chewing, injection and snorting. This represents a serious problem given the large number of legitimate prescriptions written in the U.S.; for example, the medical use of opioids within the U.S. increased 400% from 1996 to 2000.

The problems with abuse are significant and longstanding, and efforts to design new abuse resistant or abuse deterrent formulations have been largely unsuccessful. U.S. Pat. No. 3,980,766 describes the incorporation of an ingestible solid which causes a rapid increase in viscosity (gelling) upon concentration of an aqueous solution thereof. U.S. Pat. No. 4,070,494 describes the incorporation of a non-toxic, water gelable material in an amount sufficient to render the drug resistant to aqueous extraction, thus retarding the release of the drug substance. U.S. Pat. No. 6,309,668 describes a tablet for oral administration containing two or more layers comprising one or more drugs and one or more gelling agents within separate layers of the tablet. The examples in this patent all describe conventional immediate release formulations and the resulting tablets form a gel when combined with the volume of water necessary to dissolve the drug; this formulation thus reduces the extractability of the drug from the tablet. It should be noted that although these compositions may preclude abuse by injections, this approach would fail to prevent abuse by crushing and swallowing or snorting the formulation, which are commonly reported methods of abuse associated with OXYCONTIN®.

U.S. Pat. Nos. 6,277,384, 6,375,957 and 6,475,494 describe oral dosage forms including a combination of an orally active opioid agonist and an orally active opioid antagonist in a ratio that, when delivered orally, is analgesically effective but that is aversive in a physically dependent subject. While such a formulation may be successful in deterring abuse, it also has the potential to produce adverse effects in legitimate patients.

U.S. Patent Application Publication No. 2007/0066537 discloses an abuse resistant opioid wherein the opioid is bound to niacin, biotin or peptide.

U.S. Patent Application Publication No. 2006/0104909 discloses a pharmaceutical composition comprising an opioid and a tamper-resistant matrix comprising one or more tenacious cross-linked polymers that are capable of bonding with the opioid such that the opioid is substantially incapable of immediate release from the polymer. A further preferred aspect uses a water insoluble matrix material comprising a pH insensitive material such as ethylcellulose, cellulose acetate, vinyl acetate/vinyl chloride copolymers, acrylate/methacrylate copolymers, polyethylene oxide, hydroxypropyl methylcellulose, hydroxyethyl cellulose, hydroxypropyl cellulose, triglycerides, hydrogenated vegetable oils, triglyceride polyalkoxyalkylesters, fats, waxes and water insoluble partially-degraded proteins. The surface coating material comprises a hydrophobic polymer such as a pharmaceutically acceptable acrylic polymer such as acrylic acid and methacrylic acid copolymers, methyl methacrylate copolymers, ethoxyethyl methacrylates, cyanoethyl methacrylate, aminoalkyl methacrylate copolymer, poly (acrylic acid), polymethacrylic acid, methacrylic acid alkylamide copolymer, poly(methyl methacrylate), poly(methacrylic acid anhydride), methyl methacrylate, polymethacrylate, polyacrylamide and glycidyl methacrylate copolymers. In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

U.S. Patent Application Publication No. 2005/0281748 discloses an opioid bound to a lipid or fatty acid to produce an abuse resistant drug.

It is an object of the present invention to provide a pharmaceutical composition that significantly reduces the potential for improper administration or use of drugs but which, when administered as directed, is capable of delivering a therapeutically effective dose. In particular, the present invention addresses the need for a drug product which, compared to conventional formulations, decreases the intensity, quality, frequency and rate of occurrence of the "euphoria" effect which can occur with improper administration.

SUMMARY OF THE INVENTION

The present invention relates to an abuse resistant oral pharmaceutical composition, comprising: a barrier layer, comprising a first polymer; and a diffusion layer, comprising a second polymer, substantially covering the barrier layer, wherein the diffusion layer is bonded to the barrier layer and comprises a drug that is substantially homogeneously distributed within the second polymer and diffuses from the diffusion layer within the gastrointestinal (GI) tract. The pharmaceutical composition may optionally comprise an expansion layer comprising an expandable polymer and wherein the barrier layer substantially covers the expansion layer.

The present invention also relates to an oral pharmaceutical composition, comprising a drug in a pharmaceutically effective amount, wherein the pharmaceutical composition in configured such that when the pharmaceutical composition is administered in physically compromised form to a subject, the rate of drug released from the composition within a time period selected from the group consisting of 2 hours, 4 hours, 8 hours and 16 hours is substantially the same or lower than the rate of drug released when the pharmaceutical composition is administered in an intact form.

The present invention also relates to an oral pharmaceutical composition, comprising a drug in a pharmaceutically effective amount, wherein the pharmaceutical composition is configured such that when the pharmaceutical composition is administered in physically compromised form to a subject, the amount of drug released from the composition within a time period selected from the group consisting of 2 hours, 4 hours, 8 hours and 16 hours, is substantially the same or lower, preferably less than 20%, more preferably less than 30%, and most preferably less than 40%, than the amount of drug released when the pharmaceutical composition is administered in an intact form. In the context of this application, the phrase "substantially the same" means within (+/−) 30%, preferably within (+/−) 20%, and more preferably within (+/−) 10%.

The present invention also relates to an oral pharmaceutical composition, comprising a drug in a pharmaceutically effective amount, wherein the pharmaceutical composition in configured such that when the pharmaceutical composition is contacted with an alcohol or consumed with an alcohol, the rate of drug released from the composition within a time period selected from the group consisting of 2 hours, 4 hours, 8 hours and 16 hours, is substantially the same or lower, preferably less than 40%, more preferably less than 30%, and most preferably less than 20%, than the rate of drug released when the pharmaceutical composition is administered without an alcohol.

The present invention also relates to an oral pharmaceutical composition, comprising a drug in a pharmaceutically effective amount, wherein the pharmaceutical composition is configured such that when the pharmaceutical composition is administered in an intact form at least 50% of the amount of drug is released after 8 hours and when the pharmaceutical composition is administered in physically compromised form no more than 40%, preferably no more than 30%, of the amount of drug is released after 1 hour.

The present invention also relates to an oral pharmaceutical composition, comprising a drug in a pharmaceutically effective amount, wherein the pharmaceutical composition is configured such that when the pharmaceutical composition is administered in an intact form at least 90% of the amount of drug is released after 1 hour and when the pharmaceutical composition is administered in physically compromised form no more than 75% of the amount of drug is released after 1 hour.

The present invention also relates to a method of making an abuse resistant oral pharmaceutical composition, comprising: forming a barrier layer, wherein the barrier layer comprises a first polymer; and applying a diffusion layer over the barrier layer to substantially cover the barrier layer, wherein the diffusion layer comprises a second polymer and a drug that is homogeneously distributed within the second polymer; and bonding the diffusion layer to the barrier layer, preferably by physical bonding.

The present invention also relates to a method of making an abuse resistant oral pharmaceutical composition, comprising: forming an expansion layer comprising an expandable polymer; applying a barrier layer over the expansion layer to substantially cover the expansion layer, wherein the barrier layer comprises a first polymer; and applying a diffusion layer over the barrier layer to substantially cover the barrier layer, wherein the diffusion layer comprises a second polymer and a drug that is homogeneously distributed within the second polymer; and bonding the diffusion layer to the barrier layer, preferably by physical bonding. In some embodiments, the barrier layer can be applied onto the expansion layer by spraying or dry coating.

The present invention also relates to a method of treating a condition, comprising administering to a patient in need thereof the pharmaceutical composition of the invention.

The present invention also relates to an oral pharmaceutical composition, comprising a drug in a pharmaceutically effective amount, wherein the pharmaceutical composition is configured such that when the pharmaceutical composition is administered in physically compromised form to a subject, the intensity of the euphoria is substantially the same or lower than the intensity of the euphoria achieved after administration of a physically compromised bioequivalent composition not comprising means for deterring abuse.

DESCRIPTION OF THE PREFERRED EMBODIMENTS

Figure 1:
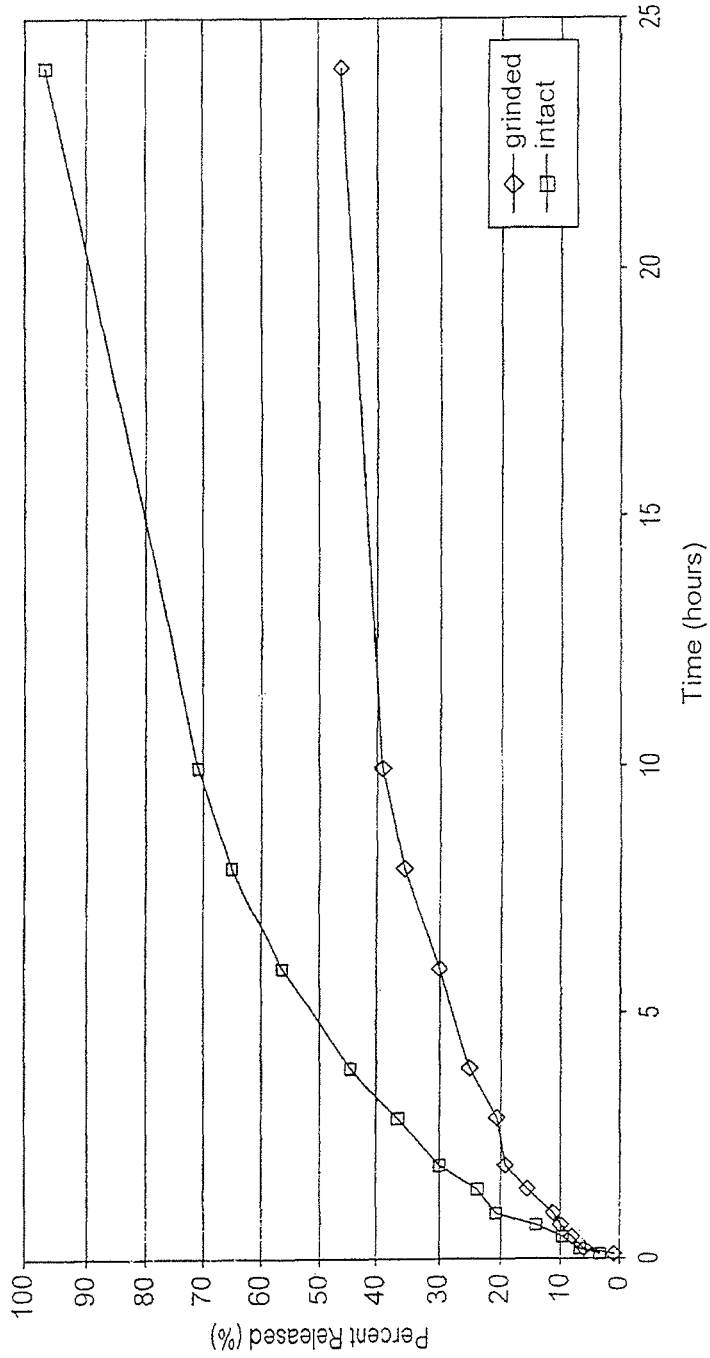
FIG. 1 is a graph of percent release rate versus time of a tablet made according to Example 31 when taken properly (intact) as compared to a ground form of the same tablet formulation.
Figure 2:
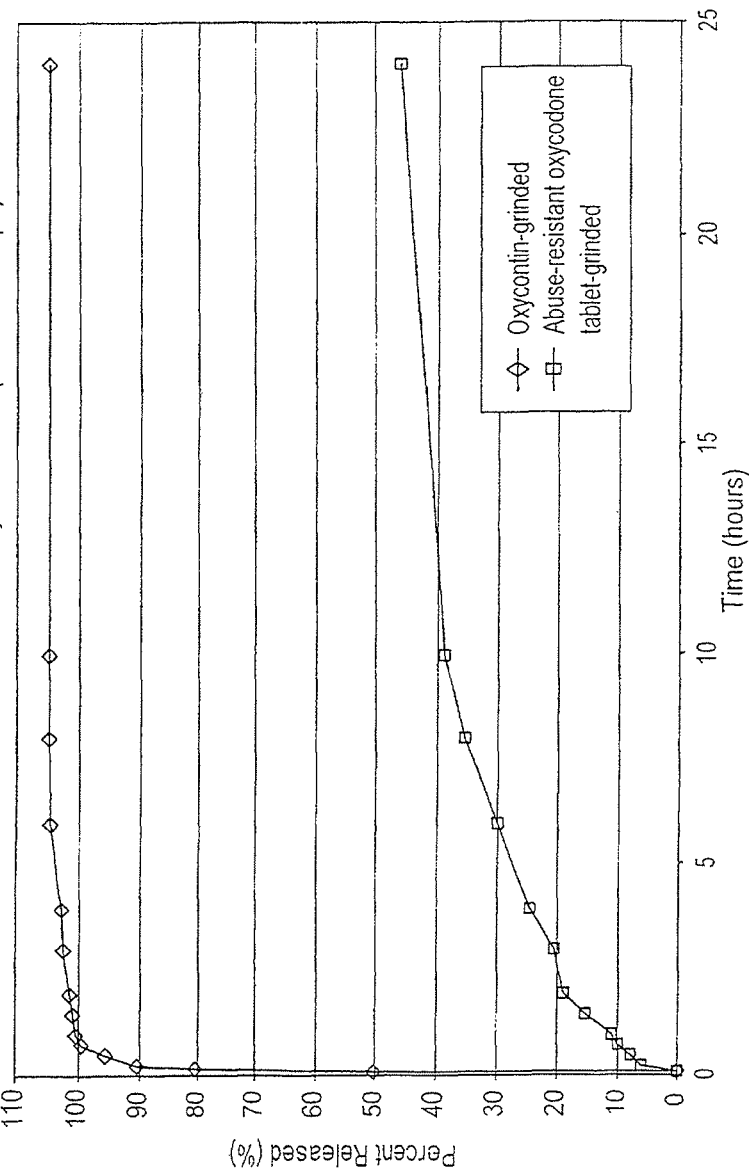
FIG. 2 is a graph of percent release rate versus time of a ground tablet of OXYCONTIN® versus a ground tablet of the formulation of Example 31.
Figure 3:
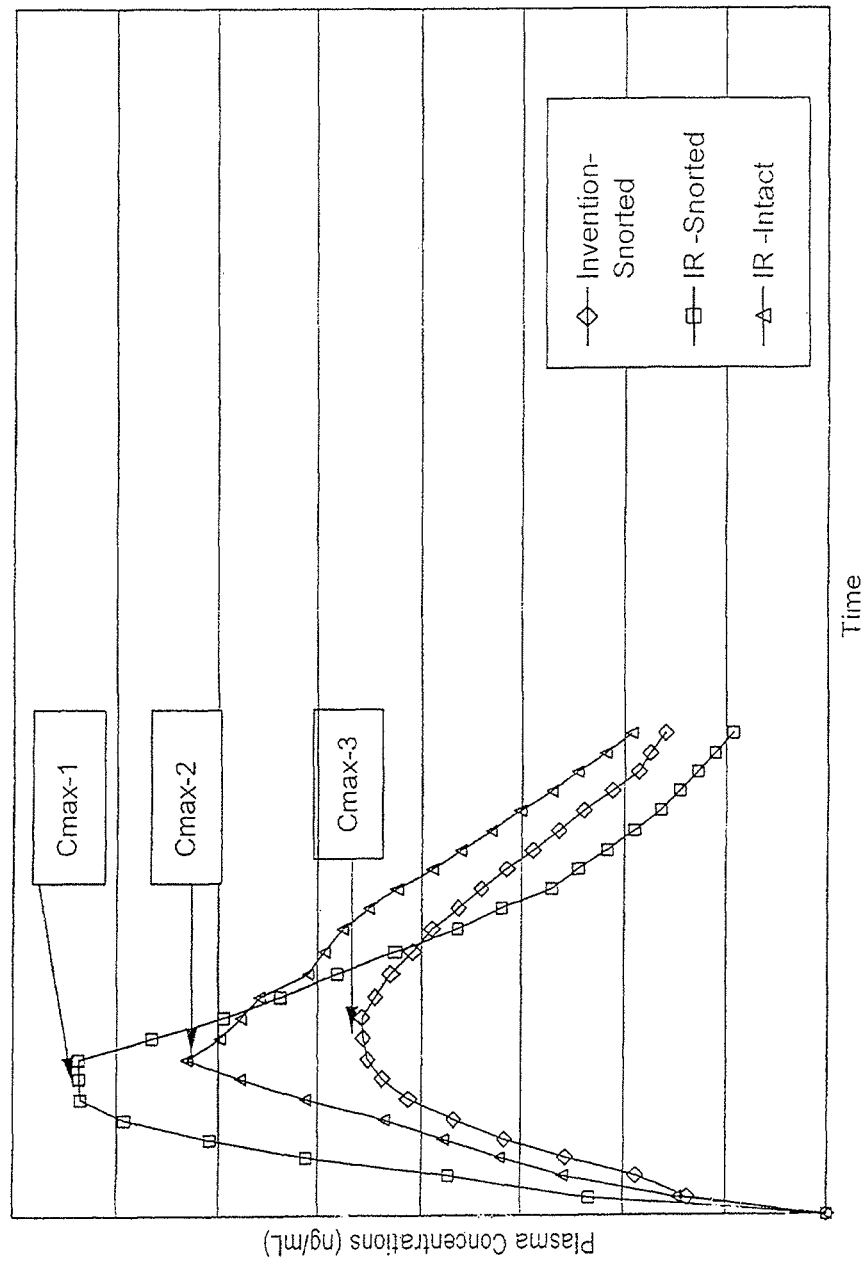
FIG. 3 is an in vivo simulation showing features of the invention, prepared utilizing the Microsoft Excel software program. Currently marketed immediate or extended release tablets would exhibit Cmax−1 as shown after grinding the tablets and subsequently snorting the ground powder. The same tablets when ingested intact would show Cmax−2, as the rate of absorption will be delayed due to physiological factors in the GI tract. A bioequivalent tablet formulation of the invention would show the same profile as the Cmax−2 curve. However, the tablets of the current invention when ground and snorted would show the lower Cmax−3.

The concept behind the present invention of an abuse resistant pharmaceutical composition is to provide the necessary amount of a drug to the patient to accomplish the pharmaceutical effect (such as pain relief), while decreasing the ability of a potential abuser to alter the composition in order to experience a "high" or to induce rapid death. Drugs which are typically abused, and therefore are suitable for the present invention, include pain medications, such as opioids, anxiety attack medications, sleeping medication, and stimulants, among others.

The abuse deterrent composition of the invention can retard, or at least not increase significantly, the release of the drug substance from a dosage form when the physical integrity of the dosage form containing the composition is compromised and the resulting formulation is subsequently snorted, injected, or swallowed. The composition is "physically compromised" when it is in a form other than an intact form. This can be achieved by various means such as by chewing, chopping, grinding, crushing, or placing into solvents, such as those containing an alcohol (e.g., ethyl alcohol) and/or water. The composition of the invention thus provides a deterrent to common methods of improper administration, including intravenous injection of the drug dissolved in solvent, and nasal or oral administration of the crushed formulation, as the drug will not be immediately and rapidly released from the formulation and as the actual amount of drug release can be decreased as compared to an intact formulation. When administered as directed, the drug substance is released more gradually from the composition within the gastrointestinal (GI) tract, preferably by dissolution and/or diffusion mechanisms.

According to one embodiment, the abuse resistant pharmaceutical composition of the present invention comprises: a barrier layer, comprising a first polymer; and a diffusion layer, comprising a second polymer, substantially covering the barrier layer, wherein the diffusion layer is bonded to the barrier layer and comprises a drug that is substantially homogeneously distributed within the second polymer and diffuses from the diffusion layer within the gastrointestinal tract. The pharmaceutical composition optionally comprises an expansion layer comprising an expandable polymer. In embodiments wherein the pharmaceutical composition comprises an expansion layer, the barrier layer substantially covers the expansion layer.

The abuse deterrent composition of the invention can comprise either or both extended release formulations, with a typical in vivo or in vitro slow release of drug over a period of about 6 to about 24 hours, preferably at least 80% of the drug released at about 12 to about 24 hours, as well as immediate release formulations, preferably with a release of at least 80%, more preferably at least 90% and most preferably at least 95%, of the drug in one hour, designed for oral administration.

The abuse resistant oral pharmaceutical composition can be in any pharmaceutical dosage form, including, but not limited to a tablet, a capsule, a micro tablet, granules, pellets, a lollipop, a lozenge and a coated capsule. In preferred embodiments, the abuse resistant oral pharmaceutical composition is in a tablet dosage form.

In embodiments where the abuse resistant oral pharmaceutical composition comprises the optional expansion layer, the expansion layer is the innermost of the three layers of the drug composition. The expansion layer is preferably an inert layer, which does not contain any drug, and it comprises an expandable polymer. The expansion layer preferably has a thickness of about 0.5 to 15 mm, more preferably about 2 to 12 mm, and most preferably about 4 to 10 mm. The thickness of the expansion layer is preferably about 5 to 95%, more preferably about 40% to 95%, and most preferably about 50% to 90% of the thickness of the tablet.

In some embodiments, when the expandable polymer of the optional expansion layer is exposed to liquids, preferably liquids comprising water and/or an alcohol such as ethyl alcohol, the expandable polymer absorbs the liquid, and preferably expands and/or forms is a gel. It is preferably a hydrophilic polymer, most preferably a hydrophilic polymer that swells upon contact with liquids and/or gels. In a preferred form, when the expansion layer is exposed to a liquid after the abuse deterrent composition is physically compromised and fragments of the composition containing the expansion layer are formed, the expandable polymer absorbs at least a portion of the liquid and forms a gel. Preferably the gel further retards release of the drug from the diffusion layer. Further, the increased viscosity may make it difficult for an abuser to draw up the formulation into a syringe for injection. The expansion layer preferably comprises a polymer present in the range of 5 to 90% by weight, based on the total weight of the dosage form.

Typical agents employed in the expansion layer include, but are not limited to methylcellulose, sodium carboxymethylcellulose, methylhydroxyethylcellulose, methylhydroxypropylcellulose, alginic acid, polyacrylic acid, and tragacanth, or a combination of two or more of these substances. Most preferred are hydroxypropyl methylcellulose, which is sometimes marketed under the tradename METHOCEL® and polyacrylic acid, which is sometimes marketed under the tradename CARBOPOL®.

The expansion layer may also include a disintegrant such as croscarmellose sodium or sodium starch glycolate, to help assure the expansion layer quickly disperses in a liquid. Additional ingredients which may be present in the expansion layer include, but are not limited to fillers, dyes, lubricants or water permeation enhancers such as sodium chloride. The use of highly soluble polymers, disintegrants or combinations thereof is generally known in the pharmaceutical arts, and as would be understood to one skilled in the art, any suitable highly soluble polymer or disintegrant or equivalent substances may be used in conjunction with the present invention and embodiments thereof.

The barrier layer is interior to the diffusion layer. In some embodiments wherein the pharmaceutical composition comprises an expansion layer, the expansion layer is the innermost of the three layers and the barrier layer substantially covers the expansion layer. Substantial covering of the expansion layer means that more that 80%, more preferably more than 90%, and most preferably more than 95% of the expansion layer is covered by the barrier layer. 100% coverage is most suitable.

The barrier layer preferably has a thickness of about 0.1 to 2.5 mm, more preferably about 0.2 to 2.0 mm, and most preferably about 0.5 to 1.5 mm. The thickness of the barrier layer is preferably about 5 to 50%, more preferably about 8 to 30%, and most preferably about 10 to 25% of the total thickness of the composition.

The barrier layer serves a number of functions. For example, the barrier layer acts as barrier between the diffusion layer and the expansion layer, decreasing the amount of liquid that can enter into the expansion layer when the dosage form is in an intact form. Further, the barrier layer acts to improve the mechanical strength of the composition.

The barrier layer comprises a polymer. Typical barrier layer polymers include, but are not limited to, polyacrylates and the copolymers thereof (such as those marked under the tradename EUDRAGIT® NE 30 D (ethyl acrylate/methyl methacrylate copolymer, preferably as an aqueous dispersion comprising about 30% ethyl acrylate/methyl methacrylate copolymer (ratio 2:1) and 1.5% NONOXYNOL® (emulsifier)), EUDRAGIT® FS 30 D (poly(methyl acrylate-co-methyl methacrylate-co-methacrylic acid) 7:3:1), EUDRAGIT® RS 30 D (poly(ethyl acrylate-co-methyl methacrylate-co-trimethylammonioethyl methacrylate chloride) 1:2:0.1), SURELEASE® (aqueous ethylcellulose dispersion type B NF) from COLORCON®, AQUACOAT® (ethylcellulose aqueous dispersion, cellulose acetate phthalate aqueous dispersion) from FMC®, and mixtures of EUDRAGIT® NE 30 D and AQUACOAT®, polyethylene glycol, polyethylene oxides, polyethylenes, polypropylenes, polyvinyl chlorides, polycarbonates, polystyrenes, and the like. The preferred polymers of the barrier layer are polyacrylate and polyethylene glycol and in particular, a polyacrylate dispersion. In embodiments wherein the pharmaceutical composition comprises an expansion layer, the barrier layer may also contain an adhesion agent to help it adhere to the expansion layer. The use of polymers resistant to biodegradation, adhesion agents or combinations thereof is generally known in the pharmaceutical arts, and as would be understood to one skilled in the art, any suitable bioresistant polymer or adhesion enhancing agent may be used in conjunction with the present invention and embodiments thereof.

Preferably, when a dosage form containing the abuse deterrent pharmaceutical composition of the present invention is administered to a subject in the intact form, the barrier layer polymer does not substantially dissolve in the GI tract, mucous membranes, blood vessels or lungs. Rather, the barrier layer polymer passes through the body in a substantially undissolved form. "Substantially undissolved" means that less than 30%, more preferably less than 20% and most preferably less than 10% of the polymer is dissolved.

The diffusion layer substantially covers the barrier layer. Substantial covering of the barrier layer means that more that 80%, more preferably more than 90%, and most preferably more than 95% of the expansion layer is covered by the barrier layer. 100% coverage is most suitable.

The diffusion layer comprises a polymer and a drug, preferably a drug which is substantially homogeneously distributed in the polymer. "Substantially homogeneously distributed" means that more that 80%, more preferably more than 90%, and most preferably more than 95% of the drug is homogeneously distributed. The polymer and drug dispersion of the diffusion layer is applied and bonded to the barrier layer.

The diffusion layer preferably is a thin layer with a large surface area relative to the thickness of the layer. The diffusion layer preferably has a thickness of about 0.1 to 1.0 mm, more preferably about 0.15 to 0.7 mm, and most preferably about 0.2 to 0.4 mm. The thickness of the diffusion layer is preferably about 1 to 30%, more preferably about 2 to 20%, and most preferably about 3 to 10% of the thickness of the tablet. In the preferred embodiments of this invention, the diffusion layer is relatively thin as compared to the surface area of the diffusion layer.

In some preferred embodiments, one or more of the layers can contain dye which, when in contact with liquid or mouth saliva, will produce a stain or color. This could aid in abuse resistant characteristics of the tablets of the present invention. Examples of dyes include, but are not limited to, FD&C Red #3, FD&C Red #28 and FD&C Blue #1.

The drug incorporated in the pharmaceutical compositions of the invention can be any drug, or any combinations of two or more drugs. However, typically, the drug or drugs will be one that is often abused, such as central nervous system stimulants and depressants. Examples of central nervous system stimulants include, but are not limited amphetamines and agents such as cocaine. Examples of central nervous depressants include, but are not limited to, opioids, barbiturates, benzodiazepines, and other anxiety and sleep medications. Examples of combinations of two drugs include oxycodone and morphine.

Examples of opioids include, but are not limited to the following: alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, and tramadol. Any opioid or pharmaceutically acceptable salt or ester thereof may be used in the abuse deterrent composition. Preferred opioids include fentanyl, sufentanil, carfentanil, lofentanil, alfentanil, hydromorphone, oxycodone, morphine, hydroxycodone, propoxyphene, pentazocine, methadone, tilidine, butorphanol, buprenorphine, levorphanol, codeine, oxymorphone, meperidine, and dihydrocodeinone. More preferred opioids include oxycodone, hydrocodone, codeine, morphine, oxymorphone and hydromorphone, and pharmaceutically acceptable salts and esters thereof. The most particularly preferred opioids are oxycodone and morphine and pharmaceutically acceptable salts thereof.

Examples of barbiturates include, but are not limited to mephobarbital (which is sometimes marketed under the tradename MEBARAL®) and pentobarbital sodium (which is sometimes marketed under the tradename NEMBUTAL®). Barbiturates are often prescribed to treat anxiety, tension, and sleep disorders.

Examples of benzodiazepines and benzodiazepine derivatives include, but are not limited to diazepam (sometimes marketed under the tradename VALIUM®), alprazolam (sometimes marketed under the tradename XANAX®), triazolam (HALCION®), and estazolam (PROSOM®). Benzodiazepines are often prescribed to treat anxiety, acute stress reactions, and panic attacks.

An example of another CNS depressant is zaleplon, which is sometimes marked under the tradename SONATA®.

Although the various classes of CNS depressants work differently, they all can produce a beneficial drowsy or calming effect in individuals suffering from such conditions as sleep disorders and anxiety. However, if one uses these drugs over a long period of time, the body can develop tolerance, and larger doses may be needed to achieve the initial effects. In addition, continued use can lead to physical dependence and, when use is reduced or stopped, withdrawal symptoms. Both barbiturates and benzodiazepines have the potential for abuse and should be used only as prescribed. As with opioids, an overdose of these drugs can be fatal.

Stimulants increase heart rate, blood pressure and metabolism, sometimes providing feelings of exhilaration and energy and increased mental alertness. Amphetamines such as methylphenidate (sometimes marketed under the tradename RITALIN®) and dextroamphetamine (sometimes marketed under the tradenames ADDERALL® and DEXEDRINE®) are often prescribed for the treatment of narcolepsy, attention-deficit/hyperactivity disorder, and depression that has not responded to other treatments. They also may be used for short-term treatment of obesity. Individuals may become addicted to the sense of well-being and enhanced energy that stimulants can generate. Taking high doses of stimulants repeatedly over a short time, however, can lead to feelings of hostility or paranoia. Additionally, taking high doses of stimulants may result in dangerously high body temperatures and an irregular heartbeat.

Preferred embodiments of the invention include a drug and amounts as follows: oxycodone or a pharmaceutically acceptable salt thereof, which is present in an amount of about 5 mg to about 400 mg; morphine or a pharmaceutically acceptable salt thereof, which is present in an amount of about 15 mg to about 800 mg; hydromorphone or a pharmaceutically acceptable salt thereof, which is present in an amount of about 1 mg to about 64 mg; hydrocodone or a pharmaceutically acceptable salt thereof, which is present in an amount of about 5 mg to about 400 mg; and oxymorphone or a pharmaceutically acceptable salt thereof, which is present in an amount of about 4 mg to about 80 mg.

In addition to one or more drugs, the diffusion layer contains one or more polymers. Examples of polymers which can be used in the diffusion layer include, but are not limited to, ethyl cellulose, a quaternary ammonium acrylic or methacrylic polymers, an acrylic or a methacrylic ester copolymers or a mixture thereof, which can also be used as sustained release agents. Common tradenames include various grades of EUDRAGIT®s (all from Röhm), and SURE- LEASE® (from COLORCON®). The preferred polymers of the diffusion layer are acrylic or methacrylic polymers and particularly ethyl acrylate or methyl methylacrylate dispersions. The use of diffusion polymers, preferably gradually abrading polymers, is generally known in the pharmaceutical arts, and as would be understood to one skilled in the art, any suitable gradually abrading polymers or agent may be used in conjunction with the present invention and embodiments thereof.

Suitable waxes may replace a portion or all of the polymer in the diffusion layer. Suitable waxes include both synthetic and natural waxes, as well as wax-like substances, fats and fatty substances, hydrocarbons like paraffin, beeswax, carnauba wax, and the like, including combinations of these substances. These substances dissolve very slowly or not at all in the GI tract. The use of wax-like substances is generally known in the pharmaceutical arts, and as would be understood to one skilled in the art, any suitable wax-like substances may be used in conjunction with the present invention and embodiments thereof.

The diffusion layer may optionally also contain sustained or extended release and/or enteric coating. Examples of such materials are cellulose acetate phthalate, hydroxypropyl methylcellulose phthalate, polyvinyl acetate phthalate, methacrylic acid:acrylic ester copolymer, hydroxypropyl methylcellulose acetate succinate, shellac, cellulose acetate trimellitate, and mixtures thereof. The diffusion layer may also contain water-soluble polymers such as polyvinylpyrrolidone, hydroxypropyl cellulose, hydroxypropyl methylcellulose, polyethylene glycol having a molecular weight of from 1,700 to 20,000 and polyvinyl alcohol and monomers therefor and mixtures thereof. The use of sustained, extended and enteric coating materials is generally known in the pharmaceutical arts, and as would be understood to one skilled in the art, any suitable sustained, extended and enteric coating materials or similar agents may be used in conjunction with the present invention and embodiments thereof.

In the preferred embodiments, for the barrier as well as the diffusion layer, the acrylic coating is an acrylic lacquer used in the form of an aqueous dispersion that is commercially available from Röhm Pharma under the tradename EUDRAGIT®.

The substantially homogeneous distribution of drug within the polymer of the diffusion layer allows for the release of drug at a defined desired rate within the GI tract, for example, such that it slowly releases the drug. The diffusion layer may be an immediate release layer or an extended release layer. The diffusion layer preferably maintains the same release profile, preferably up to 24 hours, as conventional intact formulations, even when the layer is broken up into smaller pieces. The presence of the drug in the diffusion layer is thought to contribute to the formation of pores in the polymers of the diffusion layer. The presence of pores allows for the gradual erosion of the diffusion layer and release of the drug. The release rate of drug can be adjusted by changing the polymer pore size. For example, reduction in polymer pore size can reduce the release rate of the drug. Stretching or exposing the diffusion layer to solvents will also reduce polymer pore size and reduce the release rate of the drug.

The diffusion and barrier layers are bonded to each other. The layers may be bonded by any method known in the art. In some embodiments, the layers are chemically bonded, or preferably, they are physically bonded. In preferred embodiments, a physical bond is formed between layers by heat curing. In another preferred embodiment, the layers are in powder form and are physically bonded by using a tablet press. In some embodiments, the expansion and barrier layers may be manufactured as bulk tablets and stored for a period of time, preferably up to seven days, as long as the barrier layer is not cured.

Preferably, the composition is configured such that when the pharmaceutical composition is physically compromised and particles of the pharmaceutical composition containing the diffusion layer and the barrier layer are formed, the bond between the diffusion layer and barrier layer within the particles is substantially preserved. In the preferred embodiments of this invention, compromising the drug product in this manner will result in pieces of the diffusion layer and pieces of the barrier layer tightly bonded together within the particles resulting from the compromising activity. Thus, in the preferred embodiments of this invention, the relative surface area of the diffusion layer will increase only marginally (e.g., no more than 50%, preferably no more than 25%, most preferably no more than 10%), when particles are produced in a range of 500 mesh to 8 mesh. The control of drug diffusion surface area in the preferred embodiments of this invention prevents a rapid release of the drug product from the drug product components, even if compromised.

The formation of a bond between the diffusion layer and the barrier layer is important in achieving abuse resistance because when the dosage forms of the invention are physically compromised, the barrier layer protects the inner side of the diffusion layer, preventing significant increase in drug release. Therefore, the drug substance maintains release gradually at substantially its designed rate from the outer side of the diffusion layer.

The layer bonding design feature may be optimized by applying the diffusion layer immediately after the barrier layer is applied and then curing them together.

The diffusion layer polymer is able to hold the drug within and thus prevent the dumping of drug substance after alteration of the dosage form. The barrier layer and optional expansion layer enhance the abuse resistant feature of the pharmaceutical composition.

Other components may be added to any or all of the various layers provided that they do not interfere with the drug and provide a desired benefit to the pharmaceutical. Exemplary of such other components are: plasticizers, anti-adhesive, inert fillers, lipophilic agents and pigments used in a known manner. Tackiness of the water-dispersible film forming substance may be overcome by simply incorporating an anti-adhesive in the coating. Examples of anti-adhesive are metallic stearates, microcrystalline cellulose, calcium phosphate, AEROSIL® 200, and talc. Those of ordinary skill in the art would understand the need for and applicability of such other components to overcome manufacturing, shelf-life or release profile issues.

Examples of plasticizers for use in accordance with the present invention include triacetin, acetylated monoglyceride, olive oil, acetyl tributyl citrate, acetyl triethyl citrate, glycerin, sorbitol, polyethylene glycol, and polypropyleneglycol.

Fillers/diluents/binders may be incorporated such as sucrose, sorbitol, mannitol, various grades of lactose, various grades of microcrystalline cellulose, dextrins, maltodextrins, starches or modified starches, sodium phosphate, calcium phosphate, calcium carbonate, gelatin, polyvinylpyrrolidone, and sodium carboxymethylcellulose.

Disintegrants may be used such as cellulose derivatives, including microcrystalline cellulose, low-substituted hydroxypropyl cellulose, croscarmellose sodium, alginic acid, insoluble polyvinlypyrrolidone, and sodium carboxymethyl starch.

Glidants and lubricants may be incorporated such as stearic acid, metallic stearates, talc, waxes, and glycerides with high melting temperatures, colloidal silica, sodium stearyl fumarate, polyethyleneglycols, and alkyl sulphates.

Surfactants may be employed such as non-ionic (various grades of polysorbate); anionic such as docusate sodium and sodium lauryl sulfate, and cationic such as benzalkonium chloride. An example of an amphoteric surfactant is 1,2-diacyl-L-phosphatidylcholine. The preferred surfactants are TWEEN® 80, BRIJ®, and Nanoxyl-100.

Other appropriate pharmaceutically acceptable excipients may include colorants, flavoring agents, pH adjusting agents, solubilizing agents, wetting agents, solvent resistant agents and buffering agents.

One or more other layers may be disposed under the expansion layer, or between the expansion layer and the barrier layer or above or on top of the diffusion layer. For example, in some embodiments, the expansion layer is not in direct contact with the barrier layer, as one or more layers may be disposed between the expansion layer and the barrier layer. In other embodiments, the expansion layer can cover another layer that is disposed under the expansion layer. In some embodiments, one or more additional release layers comprising one or more additional drugs can be on top of the diffusion layer. In some embodiments, the additional release layer can be an extended release layer or an immediate release layer. In some embodiments, both an extended release layer and an immediate release layer can be on top of the diffusion layer. The one or more additional drugs can be any drug, including drugs that may be part of the diffusion layer of the composition, such as central nervous system stimulants and depressants such as opioids, barbiturates, benzodiazepines, and amphetamines. Preferably, the layer on top of the diffusion layer is an immediate release layer, and drugs in the immediate release layer include, but are not limited to acetaminophen and nonsteroidal anti-inflammatory drugs.

Because of the described features above, the abuse potential of the pharmaceutical composition of the present invention is decreased. Further, the features can in some embodiments deter a patient from cutting a dosage form into smaller pieces containing a fraction of the dosage of the intact tablet. For example, a patient seeking to cut an 80 mg tablet into four 20 mg tablet pieces would be unable to achieve the necessary therapeutic effect with the cut 20 mg tablet pieces, in comparison to uncompromised 20 mg tablets. This is the case, because in this embodiment of the invention, the cut 20 mg tablet pieces would not release the full 20 mg amount of drug in the tablet piece.

Preferably, when administered properly in an intact form, the drug is released at a desired release rate from the diffusion layer, and the remainder of the pharmaceutical composition passes through the patient's body in an inert manner, because the barrier layer prevents the remainder of the composition from being broken down in the GI tract. The desired release rate may be the release rate typically obtained from the intended use, such as described in the prescribing information associated with a commercial drug product.

In a preferred embodiment of the invention wherein the composition comprises an expansion layer, physically compromising the drug product results in the expansion layer being dispersed between particles containing diffusion layer and barrier layer components, as a component of the particles containing diffusion layer and barrier layer components, or both. Thus, in preferred embodiments of the invention, once exposed to bodily fluids or other liquids, the particles containing the diffusion layer and barrier layer components become embedded in the swelled expansion layer, such that the net diffusion of the drug substance into such bodily fluids or other liquids occurs at substantially lower rates than those observed from the diffusion out of the uncompromised drug product.

In preferred embodiments of the invention, the resulting pharmaceutical composition will have both a mechanism to control and largely maintain the rate of diffusion of the drug substance from the drug substance containing compartments of the composition, as well as a mechanism to retard diffusion of the drug substance from the drug-substance containing compartments of the composition and to retain a substantial proportion of the drug substance once the composition is compromised and exposed, in whole or in part, to a liquid. A benefit of the invention is that it will be difficult for any person intending to abuse the drug substance by rapidly extracting the drug substance from the drug product through some kind of compromising activity and snorting, swallowing or injecting. As a result, improper administration of the present invention, compared to conventional formulations, results in a decreased intensity and quality of euphoria, as well as a decrease in the rate at which the euphoria occurs. Therefore, abusers hoping to attain a "high" or experience euphoria by improperly using the present composition may be unable to achieve the desired "high" or euphoria. Rather, a less intense effect, if any, is achieved at a much slower rate. Unless sophisticated and time-consuming extraction methods are employed, by applying the invention, a substantial share of the drug substance will become trapped in and not be separable from the resulting compromised drug product, thus reducing the overall bioavailability upon snorting, swallowing or injecting.

In preferred embodiments, the present composition, when compromised, releases substantially the same or a lower percentage of drug compared to an intact, uncompromised composition. In preferred embodiments, within a time period selected from the group consisting of 2 hours, 4 hours, 8 hours and 16 hours, a compromised composition release no more than 90%, more preferably no more than 75%, and more preferably no more than 60% of the drug compared to intact, uncompromised tablets over the same amount of time.

The mechanisms and benefits described above are measurable by conventional pharmaceutical in vivo and in vitro analytical techniques, such as in vivo plasma measurements or in vitro drug dissolution. With these techniques, the release of drug substance present in the pharmaceutical composition over time can be monitored and expressed as a released percentage of the drug substance originally present such composition. In preferred embodiments of the invention, the percentage of the drug substance released will be substantially lower when a pharmaceutical composition employing the invention is physically compromised and then tested in an in vitro dissolution test.

In discussing release characteristics of products of the invention, the dosage form comprising an effective amount of a drug has a dissolution rate in vitro that is measured by the USP Paddle Method of U.S. Pharmacopoeia, with USP Apparatus 1, at 100 rpm (basket) at 900 mL aqueous buffer at pH 1.6 and 7.2 and at 37° C.

Preferably, the in vitro release is about 5% to about 50% (by wt.) drug substance released after 1 hour, from about 20% to about 65% (by wt.) drug substance released after 4 hours, from about 35% to about 85% (by wt.) drug substance released after 8 hours and greater than 60% (by wt.) drug substance released after 16 hours; more preferably about 5% to about 40% after 1 hour, about 15% to about 60% after 4 hours; about 40% to about 80% after 8 hours; and about 50% to about 90% after 16 hours; more preferably about 10% to about 35% after 1 hour, about 15% to about 55% after 4 hours; about 35% to about 75% after 8 hours; and about 50% to about 80% after 16 hours; most preferably about 10% to about 30% after 1 hour, about 25% to about 60% after 4 hours; about 40% to about 80% after 8 hours; and about 55% to about 75% after 16 hours. The mechanisms and benefits described above are also measurable by conventional pharmacokinetic research techniques typically employed in the characterization of drug kinetics in human patients or other mammals.

The most relevant pharmacokinetic parameters for understanding the features and benefits of the invention are Cmax (maximum blood serum concentration of the drug substance and/or active metabolites) and AUC (area under the serum concentration curve: the integral of the blood serum concentration of the drug substance and/or active metabolites over time). In preferred embodiments of the invention, when the pharmaceutical composition is administered in physically compromised form to a subject, the Cmax and/or AUC achieved after a time period selected from the group consisting of 2 hours, 4, hours, 8 hours, 12 hours, 24 hours, and 48 hours after administration is substantially the same or lower, preferably about 20-75% lower, than the Cmax and/or AUC achieved when the pharmaceutical composition is administered in an intact form.

One embodiment of the invention relates to a pharmaceutical composition configured such that when the pharmaceutical composition is administered in physically compromised form to a subject, the Cmax and/or AUC resulting from the compromised drug product achieved after a time period selected from the group consisting of 2 hours, 4, hours, 8 hours, 12 hours, 24 hours, and 48 hours after administration, will be lower, preferably about 20-75% lower, than the Cmax and/or AUC resulting from an equal amount of a physically compromised bioequivalent composition that does not employ means for deterring abuse. A "bioequivalent" drug composition refers to an intact composition which contains the same drug and has an AUC and Cmax within the range of 80 to 125% of the AUC and Cmax of the reference drug composition.

Another embodiment of the invention relates to a pharmaceutical composition configured such that when the pharmaceutical composition is administered in physically compromised form to a subject, the Cmax/AUC ratio resulting from the compromised drug product achieved after a time period selected from the group consisting of 2 hours, 4, hours, 8 hours, 12 hours, 24 hours, and 48 hours after administration, will be or lower, preferably 20-75% lower, than the Cmax/AUC ratio resulting from a physically compromised bioequivalent drug product that does not comprise means for deterring abuse.

Another preferred embodiment of the invention is an oral pharmaceutical composition, comprising a drug in a pharmaceutically effective amount, wherein the pharmaceutical composition is configured such that when the pharmaceutical composition is administered in an intact form at least 50%, preferably at least 60%, of the amount of drug is released after 8 hours and when the pharmaceutical composition is administered in physically compromised form no more than 40%, preferably no more than 35%, more preferably no more than 30%, and most preferably no more than 25%, of the amount of drug is released after 1 hour. Preferably, when the pharmaceutical composition is administered in physically compromised form no more than 35%, more preferably no more than 30%, and most preferably no more than 25%, of the amount of drug is released in 15 minutes.

Another preferred embodiment of the invention is an oral pharmaceutical composition, comprising a drug in a pharmaceutically effective amount, wherein the pharmaceutical composition is configured such that when the pharmaceutical composition is administered in an intact form at least 90% of the amount of drug is released after 1 hour and when the pharmaceutical composition is administered in physically compromised form no more than 75%, preferably no more than 60%, of the amount of drug is released after 1 hour.

The present invention also relates to an oral pharmaceutical composition, comprising a drug in a pharmaceutically effective amount, wherein the pharmaceutical composition is configured such that when the pharmaceutical composition is administered in physically compromised form to a subject, the intensity of the euphoria is substantially the same or lower than the intensity of the euphoria achieved after administration of a physically compromised bioequivalent composition not comprising means for deterring abuse. Euphoria is a high or feeling of extreme elation, which is often experienced after an abuser is administered a pharmaceutical composition containing a central nervous system drug. The amount or intensity of euphoria can be measured in a number of different ways. Methods or techniques of measuring euphoria are sometimes similar to methods or techniques of measuring other conditions, such as pain. For example, the amount or intensity of euphoria can be measured in a numerical or linear scale, and the person experiencing the euphoria can quantify or rate the amount or intensity of the euphoria. For example, in some embodiments, the amount or intensity of euphoria can be measured on a scale from 0 to 10, wherein a high amount of euphoria is designated by the number 10, and no euphoria is designated by the number 0. Similarly, in some embodiments, the amount or intensity of euphoria can be measured on a linear scale, wherein one end of the line represents no euphoria, and the opposite end of the line represents a high amount of euphoria. In some embodiments, the pharmaceutical composition is configured such that when the pharmaceutical composition is administered in physically compromised form to a subject, the intensity of the euphoria is substantially the same or preferably less than 10%, more preferably less then 30%, and more preferably less than 50% than the intensity of the euphoria achieved after administration of a physically compromised bioequivalent composition not comprising means for deterring abuse.

The drug composition of the present invention is preferably independent of pH in its release profile. Further, there is preferably no significant change (preferably, less than 10% change) in the release rate of the formulation after 3 months of storage at 40° C. at 75% relative humidity, when measured by the USP basket method of U.S. Pharmacopoeia, with USP Apparatus 1, at 100 rpm (basket) at 900 mL aqueous buffer at pH 1.6 and 7.2 and at 37° C.

All references cited herein are hereby incorporated by reference in their entirety.

The following examples are employed to demonstrate and illustrate the present invention.

Example 1

Mannitol—90 mg
Microcrystalline Cellulose—50 mg
CARBOPOL® 71G—128 mg
Hydroxypropyl Methylcellulose, type 2910—128 mg
(METHOCEL™ K4M CR)
Magnesium Stearate—4 mg Procedure: Mannitol, Microcrystalline Cellulose, CARBOPOL® 71 G, and METHOCEL™ K4M CR were sifted through #20 mesh and blended in a blender for 10 minutes. Magnesium Stearate was sifted through #40 mesh and added in to the blender and mixed for 5 minutes to lubricate the blend. The final blend was compressed at 400-mg tablet weight and hardness between 8-15 kp.

Example 2

Mannitol—22.5 mg
Microcrystalline Cellulose—12.5 mg
CARBOPOL® 71G—32 mg
Hydroxypropyl Methylcellulose, type 2910—32 mg
(METHOCEL™ K4M CR)
Magnesium Stearate—1 mg Procedure: Mannitol, Microcrystalline Cellulose, CARBOPOL® 71 G, and METHOCEL™ K4M CR were sifted through #20 mesh and blended in a blender for 10 minutes. Magnesium Stearate was sifted through #40 mesh and added in to the blender and mixed for 5 minutes to lubricate the blend. The final blend was compressed at 100-mg tablet weight and hardness between 4-9 kp.

Example 3

Mannitol—135 mg
Microcrystalline Cellulose—75 mg
CARBOPOL® 71G—192 mg
Hydroxypropyl Methylcellulose, type 2910—192 mg
(METHOCEL™ K4M CR)
Magnesium Stearate—6 mg Procedure: Mannitol, Microcrystalline Cellulose, CARBOPOL® 71 G, and METHOCEL™ K4M CR were sifted through #20 mesh and blended in a blender for 10 minutes. Magnesium Stearate was sifted through #40 mesh and added in to the blender and mixed for 5 minutes to lubricate the blend. The final blend was compressed at 600-mg tablet weight and hardness between 8-15 kp.

Example 4

Mannitol—70 mg
Microcrystalline Cellulose—50 mg
CARBOPOL™ 71G—128 mg
Hydroxypropyl Methylcellulose, type 2910—128 mg
(METHOCEL™ K4M CR)
Croscarmellose sodium—20 mg (AC-DI-SOLID)
Magnesium Stearate—4 mg Procedure: Mannitol, CARBOPOL® 71 G, Microcrystalline Cellulose, METHOCEL™ K4CR, and AC-DI-SOL® were sifted through #20 mesh and blended in a blender for 10 minutes. Magnesium Stearate was sifted through #40 mesh and added in to the blender and mixed for 5 minutes to lubricate the blend. The final blend was compressed at 400-mg tablet weight and hardness between 8-15 kp.

The combination of CARBOPOL® and METHOCEL™ (Example 4) is a preferred formulation as it provided relatively rapid expansion capability. The addition of super disintegrant like AC-DI-SOL® aids in expanding capability. Also different expansion layer tablet weight as shown in example 1 through 3 produced the same desired characteristics of the expansion layer.

Example 5

Mannitol—45 mg
Microcrystalline Cellulose—25 mg
CARBOPOL™ 71G—64 mg
Hydroxypropyl Methylcellulose, type 2910—64 mg
(METHOCEL™ K4M CR)
Magnesium Stearate—2 mg Procedure: Mannitol, CARBOPOL® 71 G, Microcrystalline Cellulose, and METHOCEL™ K4CR were sifted through #20 mesh and blended in a blender for 10 minutes. Magnesium Stearate was sifted through #40 mesh and added in to the blender and mixed for 5 minutes to lubricate the blend. The final blend was compressed at 400-mg tablet weight and hardness between 8-15 kp.

Example 6

Expansion layer tablet (example 4)—370 g
EUDRAGIT®NE30D Dispersion—300 g
Calcium Stearate powder—15 g
Simethicone solids—0.15 g
Purified water—85 g Procedure: Expansion layer tablet having 400 mg unit weight were loaded in to a conventional coating pan and EUDRAGIT® NE30D, Simethicone Emulsion 30%, Calcium Stearate & Purified Water suspension was sprayed on to the expansion layer tablet using conventional coating techniques creating the barrier layer. The suspension was prepared by first adding Simethicone Emulsion into the Purified Water while mixing. After about 10 minutes of mixing, Calcium Stearate powder was added while mixing. After about 15 minutes of mixing, the Calcium Stearate suspension was homogenized for 10 minutes at a medium speed using a suitable homogenizer. In a separate container, required amount of Eudragit® NE 30 D was added and while mixing, Calcium Stearate suspension was added. The final coating suspension was mixed for about 20 minutes before spraying onto the tablets. The coated barrier layer tablets were then cured at 60° C. for 1-3 hours to stabilize the film. The cured tablets were then used for the diffusion layer. Throughout the coating process, product temperature of 30-35° C. was maintained. The spray rate range was between 2-10 g/min.

Example 7

Expansion layer tablet (example 4)—370 g
EUDRAGIT® NE 30D Dispersion—300 g
Calcium Stearate—15 g
Simethicone Emulsion solids—0.15 g
Purified water-85 g Procedure: The preparation of the coating suspension and the coating process of the barrier layer were same as the previous example. In this example the diffusion layer coat was immediately applied after barrier layer coat was over and then the tablets were cured at 60° C. for 1-3 hours. Throughout the coating process, product temperature of 30-35° C. was maintained. The spray rate range was between 2-10 g/min.

Example 8

Expansion layer tablet (example 5)—400 g
EUDRAGIT® NE 30D Dispersion—150 g

Calcium Stearate—5 g
Simethicone Emulsion solids—0.05 g
Purified water—28 g

Procedure: Expansion layer tablet having 200 mg unit weight were loaded in to a conventional coating pan. The coating suspension containing EUDRAGIT® NE30D, Calcium Stearate, Simethicone Emulsion 30% suspension and Purified Water was prepared similar to the example 6 and was sprayed on to the expansion layer tablet using conventional coating techniques, creating the barrier layer. The application of the barrier layer, diffusion layer and curing process was similar to Example 7. Throughout the coating process, product temperature of 30-35° C. was maintained. The spray rate range was between 2-10 g/min.

Example 9

Expansion layer tablet (example 3)—600 g
EUDRAGIT® NE 30D Dispersion—150 g
Aerosil 200—5 g Procedure: Expansion layer tablet having 600 mg unit weight were loaded in to a conventional coating pan and EUDRAGIT® NE30D, Aerosil 200 & Purified Water suspension was sprayed on to the expansion layer tablet using conventional coating techniques, creating the barrier layer. The coating suspension was prepared by adding Aerosil 200 into the required quantity of Eudragit® NE30D while mixing. The final coating suspension was mixed for about 20 minutes before spraying onto the tablets. The application of the barrier layer, diffusion layer and curing process was similar to Example 7 & 8. Throughout the coating process, product temperature of 30-35° C. was maintained. The spray rate range was between 2-10 g/min Example 10

Expansion layer tablet (example 2)—400 g
EUDRAGIT® NE 30D Dispersion—150 g
Talc—15 g
Purified water—50 g Procedure: Expansion layer tablet having 100 mg unit weight were loaded in to a conventional coating pan and EUDRAGIT® NE30D, Talc & Purified Water dispersion was sprayed on to the expansion layer tablet using conventional coating techniques, creating the barrier layer. The Barrier layer coating suspension was prepared by mixing Talc with the required amount of the purified water while mixing. After about 15 minutes of mixing, the suspension was homogenized for 10 minutes at a medium speed. In a separate container, Eudragit NE30D was added. While mixing, Talc suspension was added and the resulting coating suspension was mixed for about 20 minutes for spraying onto the tablets. The application of the barrier layer, diffusion layer and curing process was similar to Example 7, 8, and 9. The barrier layer separates the diffusion layer and expansion layer and also makes the tablet resistant to crushing, smashing and other physical means of applying pressure.

Example 11

Expansion layer tablet (example 4)—370 g
EUDRAGIT® NE 30D Dispersion—200 g
EUDRAGIT® RS 30D Dispersion—100 g
Talc—25 g
Purified water—142 g Procedure: Expansion layer tablet having 400 mg unit weight were loaded in to a conventional coating pan and EUDRAGIT® NE30D, EUDRAGIT® RS30D, Talc & Purified Water suspension was sprayed on to the expansion layer tablet using conventional coating techniques, creating the barrier layer. The coating suspension preparation was very similar to the previous example. It is possible to enhance the water impermeable characteristic of EUDRAGIT® NE30D polymer by incorporating EUDRAGIT® RS30D polymer in the barrier layer coating.

The barrier coated tablet strength and water impermeability characteristic was independent of anti-tacking agent such as Talc, Aerosil 200, Calcium Stearate, Magnesium Stearate and Glyceryl Monostearate. The barrier coat of 5-95 weight % of dry matter calculated based on the starting weight of the expansion layer tablet provided relatively crush resistant and water impermeable tablet. The preferred range for the barrier coat was between 10-60 weight %. The barrier coat and subsequent diffusion polymer coat were inseparable upon smashing, grinding or crushing if diffusion layer was applied immediately after the barrier coat and then cured together.

Example 12

Barrier coated tablets (example 7)—475 g
Oxycodone Hydrochloride—37 g
EUDRAGIT®NE 30D dispersion—175 g
Tween® 80—1.5 g
Aerosil® 200—2.0 g
Purified Water—100 g Procedure: After completion of the barrier coating, the diffusion layer was immediately applied in a conventional coating pan. The drug-polymer coat consisting of Oxycodone Hydrochloride, Tween® 80, Aerosil 200 and EUDRAGIT® NE30D suspension was sprayed on to the barrier coated tablet. The suspension was prepared by first adding Tween® 80 in the required amount of the Purified Water while mixing. The mixing was continued for about 10 more minutes. While mixing, Aerosil® 200 powder was added into the previous step suspension and mixed for about 10 minutes. In a separate container, required amount of Eudragit NE 30 D was added and while mixing, Oxycodone hydrochloride powder was added and mixing was continued for about 15 more minutes to achieve the homogenous suspension. While mixing, suspension-containing Tween-Aerosil was added and the final suspension was mixed for about 20 minutes before spraying onto the tablets. The diffusion layer coated tablets were then cured at 60° C. for 1-3 hours to stabilize the film. Throughout the coating process, product temperature of 30-35° C. was maintained. The spray rate range was between 5-15 g/min.

Example 13

Barrier coated tablets (example 7)—475 g
Oxycodone Hydrochloride—37 g
EUDRAGIT® NE 30D dispersion—275 g
Calcium Stearate—6 g
Simethicone Emulsion solids—0.06 g
Purified water—34.4 g Procedure: After completion of the barrier coating, the diffusion layer coat was immediately applied in a conventional coating pan. The suspension was prepared by first adding Simethicone Emulsion into the Purified Water while mixing. After about 10 minutes of mixing, Calcium Stearate powder was added while mixing. After about 15 minutes of mixing, the Calcium Stearate suspension was homogenized for 10 minutes at a medium speed using a suitable homogenizer. In a separate container, required amount of Eudragit NE 30 D was added and while mixing, Oxycodone hydrochloride powder was added and continued mixing for about 15 minutes to achieve the homogenous suspension. In this homogenous suspension, Calcium Stearate suspension was added. The final coating suspension was mixed for about 20 minutes before spraying onto the tablets. The diffusion-layered tablets were then cured at 60° C. for 1-3 hours to stabilize the film. Throughout the coating process, product temperature of 30-35° C. was maintained. The spray rate range was between 5-15 g/min.

Example 14

Barrier coated tablets (example 11)—485 g
Oxycodone Hydrochloride—74 g
EUDRAGIT® NE 30D dispersion—350 g
Tween 80—2 g
Calcium Stearate—11 g
Simethicone Emulsion solids—0.11 g
Purified water—60 g Procedure: After completion of the barrier coating, the diffusion layer was immediately applied in a conventional coating pan. The diffusion layer consisting of Oxycodone hydrochloride, EUDRAGIT® NE30D, Calcium Stearate, Simethicone Emulsion dispersion 30% and Purified Water suspension was sprayed on to the barrier coated tablet. The suspension was prepared by first adding Simethicone Emulsion into the Purified Water while mixing. After about 10 minutes of mixing, Calcium Stearate powder was added while mixing. After about 15 minutes of mixing, the Calcium Stearate suspension was homogenized for 10 minutes at a medium speed using a suitable homogenizer. In a separate container, required amount of Eudragit NE 30 D was added and while mixing, Tween® 80 was added and mixing was continued for about 10 minutes. After that, Oxycodone hydrochloride powder was added and while mixing. After about 15 minutes of mixing Calcium Stearate suspension was added. The final coating suspension was mixed for about 20 minutes before spraying onto the tablets. The diffusion-layered tablets were then cured at 60° C. for 1-3 hours to stabilize the film. Throughout the coating process, product temperature of 30-35° C. was maintained. The spray rate range was between 5-15 g/min.

Example 15

Barrier coated tablets (example 8)—450 g
Oxycodone Hydrochloride—10 g
EUDRAGIT® NE 30D dispersion—100 g
Aerosil 200—2 g
Purified water—100 g Procedure: After completion of the barrier coating, the diffusion layer was immediately applied in a conventional coating pan. The diffusion layer consisting of Oxycodone hydrochloride, EUDRAGIT® NE30D, Aerosil® 200 & Purified Water dispersion was sprayed on to the barrier coated tablet and then the diffusion layer coated tablets were then cured at 60° C. for 1-3 hours to stabilize the film. Refer to example 12 for the coating suspension preparation.

Example 16

Barrier coated tablets (example 7)—475 g
Hydrocodone Bitartrate—9.25 g
EUDRAGIT® NE 30D dispersion—155 g
AEROSIL® 200 powder—5 g
TWEEN 80®—1.5 g
Purified water—185 g Procedure: After completion of the barrier coating, the diffusion layer was immediately applied in a conventional coating pan. The diffusion layer dispersion was prepared by first adding TWEEN® 80 and AEROSIL® 200 powder into Purified water and mixing the suspension for about 10 minutes. Then Hydrocodone Bitartrate powder was added into the suspension. The suspension was mixed for about 15 minutes to achieve the uniform distribution of the drug. In a separate container add the required amount of Eudragit NE 30D. While mixing, add the active-Tween-Aerosil suspension in the Eudragit NE30D dispersion and mix for not less than 20 minutes before spraying on to the barrier coated tablet. The diffusion layer coated tablets were then cured at 60° C. for 1-3 hours to stabilize the film. Throughout the coating process, product temperature of 30-35° C. was maintained. The spray rate range was between 5-15 g/min.

Example 17

Barrier coated tablets (example 7)—475 g
Morphine Sulfate—55.6 g
EUDRAGIT® NE 30D dispersion—275 g
Aerosil 200—5.0 g
Purified water—150 g Procedure: After completion of the barrier coating, the diffusion layer was immediately applied in a conventional coating pan. The diffusion layer consisting of Morphine Sulfate, EUDRAGIT® NE30D, Aerosil 200 & Purified Water dispersion was sprayed on to the barrier coated tablet and then the diffusion layer coated tablets were then cured at 60° C. for 1-3 hours to stabilize the film. The diffusion layer dispersion was prepared by first adding AEROSIL® 200 powder into Purified water and mixing the suspension for about 10 minutes. Then add the Morphine sulfate powder into the suspension. Mix until uniform suspension is achieved. The suspension was homogenized for about 10 minutes at a medium speed. In a separate container add the required amount of Eudragit NE 30D. While mixing, add the drug-Aerosil suspension in the Eudragit NE30D dispersion and mix for not less than 20 minutes before spraying on to the barrier coated tablet.

Example 18

Barrier coated tablets (example 7)—475 g
Hydromorphone Hydrochloride—14.8 g
EUDRAGIT® NE 30D dispersion—250 g
Aerosil® 200—5.0 g
Purified water—100 g Procedure: After completion of the barrier coating, the diffusion layer was immediately applied in a conventional coating pan. The diffusion layer consisting of Hydromorphone Hydrochloride, EUDRAGIT® NE30D, Aerosil® 200 & Purified Water dispersion was sprayed on to the barrier coated tablet and then the diffusion layer coated tablets were then cured at 60° C. for 1-3 hours to stabilize the film. Throughout the coating process, product temperature of 30-35° C. was maintained. The spray rate range was between 5-15 g/min. Refer to the previous example for the preparation of the suspension.

Example 19

Barrier coated tablets (example 7)—475 g
Oxymorphone Hydrochloride—37 g

EUDRAGIT® NE 30D dispersion—220 g
Tween® 80—2.5 g
Aerosil® 200—5.0 g
Purified water—100 g Procedure: After completion of the barrier coating, the diffusion layer was immediately applied in a conventional coating pan. The diffusion layer consisting of Oxymorphone Hydrochloride, EUDRAGIT® NE30D, Tween® 80, Aerosil® & Purified Water dispersion was sprayed on to the barrier coated tablet. The diffusion layer dispersion was prepared by first adding TWEEN® 80 and AEROSIL® 200 powder into Purified water and mixing the suspension for about 10 minutes. Then Oxymorphone hydrochloride powder was added into the suspension. The suspension was mixed for about 15 minutes to achieve the uniform distribution of the drug. In a separate container add the required amount of Eudragit NE 30D. While mixing, add the active-Tween-Aerosil suspension in the Eudragit NE30D dispersion and mix for not less than 20 minutes before spraying on to the barrier coated tablet. The diffusion layer coated tablets were then cured at 60° C. for 1-3 hours to stabilize the film. Throughout the coating process, product temperature of 30-35° C. was maintained. The spray rate range was between 5-15 g/min.

Example 20

Barrier coated tablets (example 8)—475 g
Dexmethylphenidate Hydrochloride—10 g
EUDRAGIT® NE 30D dispersion—100 g
Aerosil 200—1 g
Purified water—100 g Procedure: After completion of the barrier coating, the diffusion layer was immediately applied in a conventional coating pan. The diffusion layer consisting of Dexmethylphenidate Hydrochloride, EUDRAGIT® NE30D, Aerosil 200 & Purified Water dispersion was sprayed on to the barrier coated tablet and then the diffusion layer coated tablets were then cured at 60° C. for 1-3 hours to stabilize the film. Throughout the coating process, product temperature of 30-35° C. was maintained. The spray rate range was between 5-15 g/min.

Example 21

Barrier coated tablets (example 10)—450 g
Zaleplon—20 g
EUDRAGIT® NE 30D dispersion—100 g
Aerosil® 200—1 g
Tween® 80—5 g
Purified water—100 g Procedure: After completion of the barrier coating, the diffusion layer was immediately applied in a conventional coating pan. The diffusion layer consisting of Zaleplon, EUDRAGIT® NE30D, Aerosil® 200, Tween 80, & Purified Water dispersion was sprayed on to the barrier coated tablet. The diffusion layer dispersion was prepared by first adding TWEEN® 80 and AEROSIL® 200 powder into Purified water and mixing the suspension for about 10 minutes. Then Zaleplon powder was added into the suspension. The suspension was mixed for about 15 minutes and homogenized for 10 minutes to achieve the uniform distribution of the drug. In a separate container add the required amount of Eudragit NE 30D. While mixing, add the active-Tween-Aerosil suspension in the Eudragit NE30D dispersion and mix for not less than 20 minutes before spraying on to the barrier coated tablet. The diffusion layer coated tablets were then cured at 60° C. for 1-3 hours to stabilize the film. Throughout the coating process, product temperature of 30-35° C. was maintained. The spray rate range was between 5-15 g/min.

Example 22

Barrier coated tablets (example 9)—695 g
Propranolol Hydrochloride—80 g
EUDRAGIT® NE 30D dispersion—150 g
Aerosil® 200—5 g
TWEEN® Solution—1 g
Purified water—100 g Procedure: After completion of the barrier coating, the diffusion layer was immediately applied in a conventional coating pan. The diffusion layer consisting of Propranolol hydrochloride, Aerosil® 200, TWEEN® 80, EUDRAGIT® NE30D, and Purified Water dispersion was sprayed on to the barrier coated tablet and then the diffusion layer coated tablets were then cured at 60° C. for 1-3 hours to stabilize the film. Throughout the coating process, product temperature of 30-35° C. was maintained. The spray rate range was between 5-15 g/min.

Example 23

Barrier coated tablets (example 6)—475 g
Tramadol Hydrochloride—92.6 g
EUDRAGIT® NE 30D dispersion—290 g
Tween® 80—0.5 g
AEROSIL® 200—5 g
Purified water—250 g Procedure: After completion of the barrier coating, the diffusion layer was immediately applied in a conventional coating pan. The diffusion layer consisting of Tramadol hydrochloride, EUDRAGIT® NE30D, Tween® 80, AEROSIL® 200 and Purified Water dispersion was sprayed on to the barrier coated tablet and then the diffusion layer coated tablets were then cured at 60° C. for 1-3 hours to stabilize the film. Throughout the coating process, product temperature of 30-35° C. was maintained. The spray rate range was between 5-15 g/min.

Example 24

Multi-Drug Product, Conventional Immediate-Release

Barrier coated tablets (example 8)—450 g
Oxycodone Diffusion Coat:
　Oxycodone Hydrochloride—10 g
　EUDRAGIT® NE 30D dispersion—100 g
　Aerosil® 200—1 g
　Purified water—100 g
Sub Coat, Acetaminophenone Coat and Seal Coat:
　5% HPMC solution Sub-coat-100 g
　Acetaminophenone Powder—2000 g
　10% HPMC solution—1000 g
　Purified Water—1000 g
　5% HPMC Seal coat—100 g Procedure: After completion of the barrier coating, the Oxycodone hydrochloride diffusion layer was immediately applied in a conventional coating pan. The diffusion layer consisting of Oxycodone hydrochloride, EUDRAGIT® NE30D, Aerosil® 200 & Purified Water suspension was sprayed on to the barrier coated tablet. The diffusion layer coated tablets were then cured at 60° C. for 1-3 hours to stabilize the film. Once the curing process was completed, 5% HPMC sub-coat was applied followed by Acetaminophenone coat. The Acetaminophenone HPMC-suspension was sprayed on to the tablets at 5-25 g/min. The Acetaminophenone suspension was prepared by first mixing 10% Methocel solution with the required quantity of the purified water and then suspending the active drug while mixing. The suspension was mixed for about 15 minutes and then homogenized for 10 minutes before spraying on to the tablets. Alternatively, the active drug powder can be dusted into the coating pan suing a powder feeder and 10% HPMC solution can be sprayed using a spray nozzle. The product temperature was kept around 30-35° C. Once all of the suspension was applied, HPMC seal coat was applied. The tablets were dried for 5 minutes at product temperature between 38-40° C. before discharging from the coating pan.

Example 25

Barrier coated tablets—475 g
Diffusion Layer Coating:
Oxycodone Hydrochloride—37 g
EUDRAGIT® NE 30D dispersion—275 g
Tween® 80—2.5 g
Calcium Stearate—6 g
Simethicone solids—0.06 g
Purified Water—34.4 g
Sustained-Release Layer Coating:
EUDRAGIT® NE 30D dispersion—30 g
HPMC 10% Solution—30 g
Aerosil® 200—2.5 g
Purified Water—66 g After completion of the barrier coating, the diffusion layer was immediately applied in a conventional coating pan. The diffusion layer consisting of Oxycodone hydrochloride, EUDRAGIT® NE30D, Tween® 80, Calcium Stearate, Simethicone Emulsion 30% dispersion and Purified Water suspension was sprayed on to the barrier coated tablet followed by the sustained-release coating suspension. The sustained-release coating suspension was prepared by mixing (about 15 minutes) Eudragit® NE 30D, 10% HPMC solution, Aerosil®200 and Purified Water. After the completion of the coating, the coated tablets were then cured at 60° C. for 1-3 hours to stabilize the film. Throughout the coating process, product temperature of 30-35° C. was maintained. The spray rate range was between 5-15 g/min.

Example 26

Diffusion Layer tablets (example 13)—600 g
Opadry 85F18422 White Powder—50 g
Purified Water—250 g After completion of Diffusion coat, the color coat is immediately applied in a conventional coating pan. The Color coating suspension is prepared by suspending Opadry powder in Purified water. About 300 g of Color Suspension is sprayed onto the diffusion layer coated tablets at a spray rate of 5-15 g/min. The product temperature of 36-38° C. is maintained throughout the process.

Example 27

Barrier coated tablets (example 8)—450 g
Oxycodone Hydrochloride—10 g
Morphine Sulfate—20 g
EUDRAGIT®NE 30D dispersion—125 g
Tween® 80—1.0 g
Aerosil® 200—2.0 g
Purified Water—100 g Procedure: After completion of the barrier coating, the diffusion layer was immediately applied in a conventional coating pan. The drug-polymer coat consisting of Oxycodone Hydrochloride, Morphine Sulfate, Tween® 80, Aerosil® 200 and EUDRAGIT® NE30D suspension was sprayed on to the barrier coated tablet. Throughout the coating process, product temperature of 30-35° C. was maintained. The spray rate range was between 5-15 g/min.

Example 28

Barrier coated tablets (example 7)—475 g
Oxycodone Hydrochloride—9.3 g
Morphine Sulfate—18.5 g
EUDRAGIT®NE 30D dispersion—275 g
Tween® 80—2.0 g
Aerosil® 200—2.5 g
Purified Water—100 g Procedure: After completion of the barrier coating, the diffusion layer was immediately applied in a conventional coating pan. The drug-polymer coat consisting of Oxycodone Hydrochloride, Morphine Sulfate, Tween® 80, Aerosil® 200 and EUDRAGIT® NE30D suspension was sprayed on to the barrier coated tablet. Throughout the coating process, product temperature of 30-35° C. was maintained. The spray rate range was between 5-15 g/min.

Example 29

Abuse-Resistant Capsule Formulation

| Expansion layer | |
|---|---|
| Mannitol - | 52.5 mg |
| Microcrystalline Cellulose- | 37.5 mg |
| Carbopol 71G - | 96 mg |
| Hydroxypropyl Methylcellulose, type 2910 - (METHOCEL ™ K4M CR) | 96 mg |
| Croscarmellose sodium - (AC-DI-SOL ®) | 15 mg |
| Magnesium Stearate - | 3 mg |
| HPMC Size # 2 Capsules - | 60 mg |
| Barrier layer | |
| EUDRAGIT ® NE 30D solids - | 97.3 mg |
| Calcium Stearate - | 16.2 mg |
| Simethicone Emulsion - | 0.2 mg |
| Purified water- | — |
| Diffusion layer | |
| Oxycodone Hydrochloride - | 40 mg |
| EUDRAGIT ® NE 30D solids - | 63.5 mg |
| Aerosil ® 200 - | 2.5 mg |
| Tween 80 ® 80 - | 1.5 mg |
| Purified water - | — |
| Sustained-Release coat | |
| EUDRAGIT ® NE 30D solids - | 15 mg |
| Aerosil ® 200 - | 2.5 mg |
| HPMC E6 solids- | 5 mg |
| Purified water - | — |
| Color coat | |
| Opadry 85F18422 Powder - | 30 mg |
| Purified Water - | — |

Procedure: Mannitol, Microcrystalline Cellulose, CARBOPOL® 71 G, and METHOCEL™ K4M CR were sifted through #20 mesh and blended in a blender for 10 minutes.

Magnesium Stearate was sifted through #40 mesh and added in to the blender and mixed for 5 minutes to lubricate the blend. The final blend was encapsulated into HPMC Size #2 Capsules at 300-mg weight. The Expansion layer Capsules were loaded in to a conventional coating pan and EUDRAGIT® NE30D, Calcium Stearate, Simethicone Emulsion & Purified Water suspension was sprayed on to the capsules creating the barrier layer. After completion of the barrier coating, the diffusion layer followed by the sustained-release coating was immediately applied in a conventional coating pan. The Sustained-release coated capsules were then cured at 60° C. for 1-3 hours to stabilize the film. After the curing process, color coat was applied. Throughout the coating process, product temperature of 30-35° C. was maintained. The spray rate range was between 5-15 g/min.

Example 30

Abuse-Resistant Pellet Formulation

| Expansion layer | |
|---|---|
| Mannitol - | 35 mg |
| Microcrystalline Cellulose- | 25 mg |
| Carbopol 71G - | 64 mg |
| Hydroxypropyl Methylcellulose, type 2910 - (METHOCEL ™ K4M CR) | 64 mg |
| Croscarmellose sodium - (AC-DI-SOL ®) | 10 mg |
| Methocel E6 solids - | 20 mg |
| Purified Water - | — |
| Barrier layer | |
| EUDRAGIT ® NE 30D solids - | 97 mg |
| EUDRAGIT ® RS 30D solids - | 32 mg |
| Talc Powder - | 50 mg |
| Purified water- | — |
| Diffusion layer | |
| Oxycodone Hydrochloride - | 40 mg |
| EUDRAGIT ® NE 30D solids - | 89 mg |
| Aerosil ® 200 - | 2 mg |
| Purified water - | — |
| Tablet Formula | |
| Avicel PH 102 - | 100 mg |
| Avicel PH 200 - | 100 mg |
| Magnesium Stearate - | 8 mg |
| Color coat | |
| Opadry 85F18422 Powder - | 30 mg |
| Purified Water - | — |

One or more active ingredients may be placed into one or more individual pellet. In some embodiments, two or more different types of pellets may be used together, wherein each type of pellet contains a different active ingredient.

Procedure: Mannitol, Microcrystalline Cellulose, CARBOPOL® 71 G, and METHOCEL™ K4M CR were sifted through #20 mesh and loaded in a Fluid Bed Dryer/Coater fitted with a Top-Spray coating nozzle. A 10% Methocel solution was sprayed as a binder solution to granulate the powder. After desired granulation was achieved, the granules are dried to moisture level of about 2%. The Dried granules are discharged from the Fluid Bed machine and sized using suitable milling machine such as Stokes Oscillating granulator. The dry-sized granules were then loaded into the same Fluid bed dryer/coater and EUDRAGIT® NE30D, Eudragit® RS 30D, Talc & Purified Water dispersion was sprayed on to the pellets/granules creating the barrier layer. After completion of the barrier coating, the diffusion layer was immediately applied. The diffusion layer consisting of Oxycodone hydrochloride, EUDRAGIT® NE30D, Aerosil® 200 and Purified Water suspension was sprayed on to the barrier coated capsules and then the diffusion layer coated pellets were cured at 60° C. for 1-3 hours to stabilize the film. Throughout the coating process, product temperature of 30-35° C. was maintained. The spray rate range was between 5-15 g/min. The Cured pellets were then blended with Avicel PH 102 and Avicel PH 200 for about 10 minutes using a suitable blender. The Magnesium stearate was added to the blender and blended for 5 minutes. The final blend was compress at 766 mg tablet weight and hardness of 8-16 kp. The Compressed tablets were then loaded into the conventional coating pan for color coating.

Example 31

| Expansion layer | |
|---|---|
| Mannitol - | 70 mg |
| Microcrystalline Cellulose- | 50 mg |
| Carbopol 71G - | 128 mg |
| Hydroxypropyl Methylcellulose, type 2910 - (METHOCEL ™ K4M CR) | 128 mg |
| Croscarmellose sodium - (AC-DI-SOL ®) | 20 mg |
| Magnesium Stearate - | 4 mg |
| Barrier layer | |
| EUDRAGIT ® NE 30D solids - | 97.3 mg |
| Calcium Stearate - | 16.2 mg |
| Simethicone Emulsion - | 0.2 mg |
| Purified water- | — |
| Diffusion layer | |
| Oxycodone Hydrochloride - | 40 mg |
| EUDRAGIT ® NE 30D solids - | 89.2 mg |
| Aerosil ® 200 - | 2 mg |
| Tween ® 80 - | 2 mg |
| Purified water - | — |
| Color coat | |
| Opadry 85F18422 Powder - | 30 mg |
| Purified Water - | — |

This formulation with respect to oxycodone was tested by comparing the release rate of a tablet made according to Example 31 when taken properly (intact) as compared to a ground form of the same tablet formulation. The results are reported in FIG. 1 and show that most of the medication is released to the patient when the tablet is properly taken.

Figure 4:
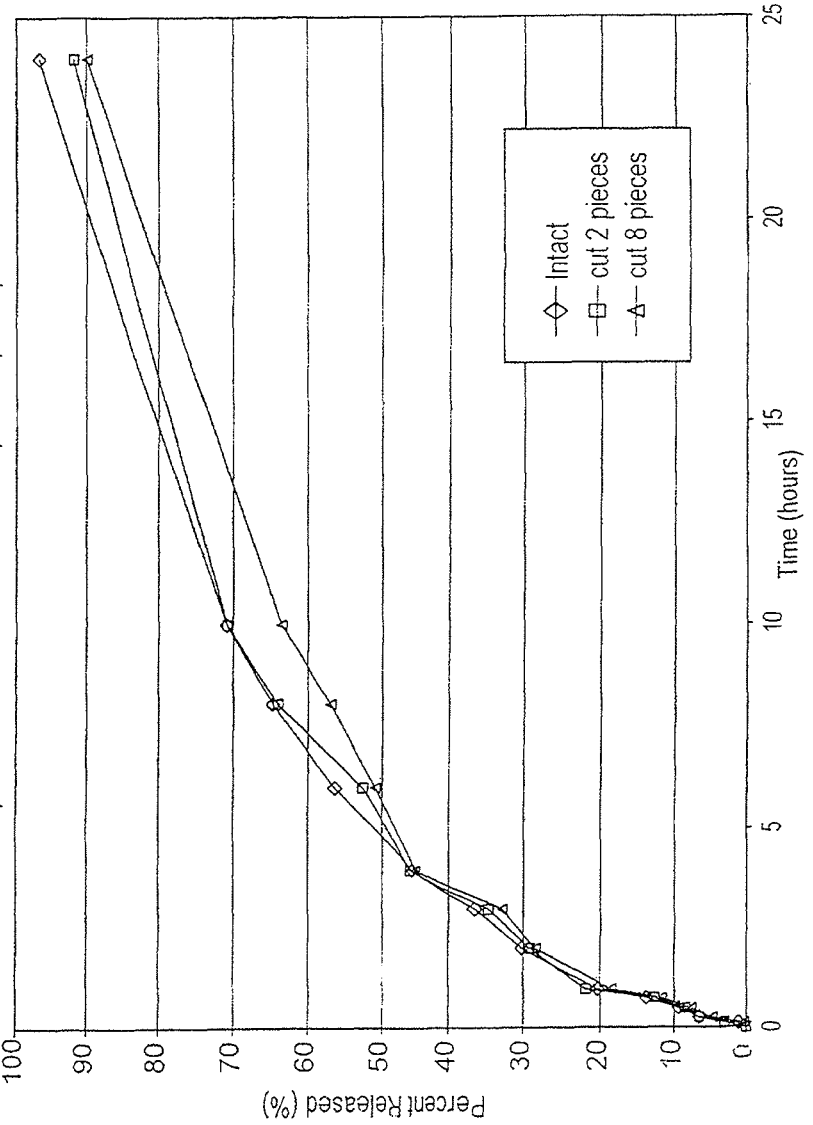
FIG. 4 is a graph of percent release rate versus time of a tablet made according to Example 31 when taken properly (intact) as compared to a "cut form" of the same tablet formulation.

Tablets comprising the pharmaceutical composition of Example 31 were cut into 2 and 8 pieces using a sharp device such as a knife and scissors. The expansion layer powder was completely removed. FIG. 4 shows the comparison of such rate. This demonstrates that when the tablets of the current invention are physically compromised, the physical bond between the diffusion layer and the barrier layer is substantially preserved. The relative surface area of the diffusion layer increases only marginally, preventing a significant increase in the drug release. Therefore, in some embodiments, even when the dosage form containing the pharmaceutical composition of the invention is physically compromised, the drug substance maintains essentially the same release profile, as compared to an intact dosage form.

What is claimed is:

1. A method of treating pain in a patient in need thereof, comprising:
orally administering to the patient an abuse resistant immediate release pharmaceutical composition containing a drug selected from the group consisting of any one or more of hydromorphone, morphine, oxycodone and pharmaceutically acceptable salts thereof in tablet dosage form, wherein the tablet dosage form comprises the following tablet layers:
an innermost expansion layer that does not contain any drug and comprises an expandable polymer selected from the group consisting of hydroxypropylmethylcellulose and polyacrylic acid,
a barrier layer that substantially covers the expansion layer and comprises a first polymer that does not substantially dissolve in the gastrointestinal (GI) tract, wherein the first polymer is selected from the group consisting of polyacrylates and polyethylene glycol, and
a diffusion layer that substantially covers and is bonded to the barrier layer and comprises said drug substantially homogeneously distributed within a second polymer selected from the group consisting of hydroxypropyl cellulose, hydroxypropylmethylcellulose, quaternary ammonium acrylic or methacrylic polymers, cellulose acetate phthalate, and polyvinyl alcohol and mixtures thereof, wherein the drug diffuses from the diffusion layer within the GI tract to treat pain,
wherein the pharmaceutical composition is configured such that when the pharmaceutical composition is physically compromised to produce particles having a particle size between 8 mesh and 500 mesh and exposed to a liquid comprising water and/or alcohol, the bond between the diffusion later and the barrier layer is substantially preserved and the expandable polymer of the expansion layer absorbs at least a portion of the liquid and expands and/or forms a gel,
wherein the diffusion layer is the only drug containing layer.

2. The method of claim 1, wherein the pharmaceutical composition is independent of pH in its release profile.

3. The method of claim 1, wherein the expansion layer further comprises a disintegrant comprising croscarmellose sodium or sodium starch glycolate.

4. The method of claim 1, where in the barrier layer covers more than 95% of the expansion layer.

5. The method of claim 1, wherein the drug is hydromorphone or a pharmaceutically acceptable salt thereof.

6. The method of claim 1, wherein the drug is oxycodone or a pharmaceutically acceptable salt thereof.

7. The method of claim 1, wherein the drug is morphine or a pharmaceutically acceptable salt thereof.

8. The method of claim 1, wherein the diffusion layer is applied immediately after the barrier layer is applied and curing them together.

9. The method of claim 1, wherein when the pharmaceutical composition is administered in intact form at least 90% of the drug is released after one hour, whereas when the pharmaceutical composition is administered in compromised form no more than 60% of the drug is released in one hour.

10. The method of claim 9, wherein the administration of the pharmaceutical composition in compromised form comprises crushing the tablet and then snorting, swallowing or injecting the crushed tablet.

11. The method of claim 9, wherein said administration in compromised form results in a reduced Cmax of the drug causing a reduced euphoria.

12. The method of claim 1, wherein the drug is morphine sulfate.

13. The method of claim 1, wherein the drug is oxycodone hydrochloride.

14. The method of claim 1, wherein the drug is hydrocodone bitartrate.

15. The method of claim 1, wherein the drug is hydrocodone hydrochloride.

* * * * *